(12) United States Patent
Tsuji et al.

(10) Patent No.: US 11,906,461 B2
(45) Date of Patent: Feb. 20, 2024

(54) ELECTRON TRANSFER BY NANOCARBON

(71) Applicants: TOYOBO CO., LTD., Osaka (JP); NATIONAL INSTITUTE OF ADVANCED INDUSTRIAL SCIENCE AND TECHNOLOGY, Tokyo (JP)

(72) Inventors: Katsumi Tsuji, Otsu (JP); Keizo Yoneda, Otsu (JP); Atsushi Sogabe, Tsuruga (JP); Atsunori Hiratsuka, Tsukuba (JP); Hitoshi Muguruma, Tsukuba (JP); Hisanori Iwasa, Tsukuba (JP); Takeshi Tanaka, Tsukuba (JP); Kouhei Orihara, Tsukuba (JP)

(73) Assignees: TOYOBO CO., LTD., Osaka (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 600 days.

(21) Appl. No.: 17/043,175

(22) PCT Filed: Mar. 29, 2019

(86) PCT No.: PCT/JP2019/014133
§ 371 (c)(1),
(2) Date: Sep. 29, 2020

(87) PCT Pub. No.: WO2019/189808
PCT Pub. Date: Oct. 3, 2019

(65) Prior Publication Data
US 2021/0293742 A1 Sep. 23, 2021

(30) Foreign Application Priority Data

Mar. 29, 2018 (JP) .................................. 2018-065464
Feb. 21, 2019 (JP) .................................. 2019-029534

(51) Int. Cl.
*G01N 27/327* (2006.01)
*C01B 32/159* (2017.01)
(Continued)

(52) U.S. Cl.
CPC ....... *G01N 27/3278* (2013.01); *C01B 32/159* (2017.08); *C01B 32/168* (2017.08);
(Continued)

(58) Field of Classification Search
None
See application file for complete search history.

(56) References Cited

U.S. PATENT DOCUMENTS

2005/0208304 A1    9/2005   Collier et al.
2010/0258033 A1   10/2010   Yang et al.
(Continued)

FOREIGN PATENT DOCUMENTS

CN    101101273 A    1/2008
CN    101151764 A    3/2008
(Continued)

OTHER PUBLICATIONS

S.G. Wang, et al., "Multi-walled carbon nanotubes for the immobilization of enzyme in glucose biosensors", Electrochemistry Communications, 5(9): p. 800-803, Sep. 2003.*
(Continued)

*Primary Examiner* — J. Christopher Ball
(74) *Attorney, Agent, or Firm* — Leydig, Voit & Mayer, Ltd.

(57) ABSTRACT

Provided is a means for promoting electron transfer between nanocarbon and other substances. An electron transfer accelerator for nanocarbon comprising a compound having an aromatic ring Skelton.

17 Claims, 12 Drawing Sheets

Specification includes a Sequence Listing.

(51) Int. Cl.

| | | |
|---|---|---|
| *C01B 32/168* | (2017.01) | |
| *C12Q 1/00* | (2006.01) | |
| *C12Q 1/32* | (2006.01) | |
| *G01N 27/30* | (2006.01) | |
| *B82Y 15/00* | (2011.01) | |
| *B82Y 40/00* | (2011.01) | |

(52) U.S. Cl.
CPC .............. *C12Q 1/005* (2013.01); *C12Q 1/32* (2013.01); *C12Y 101/05* (2013.01); *G01N 27/308* (2013.01); *B82Y 15/00* (2013.01); *B82Y 40/00* (2013.01); *C01B 2202/02* (2013.01); *C01B 2202/22* (2013.01)

(56) References Cited

U.S. PATENT DOCUMENTS

| | | | |
|---|---|---|---|
| 2010/0261072 | A1 | 10/2010 | Tsugawa et al. |
| 2012/0118761 | A1 | 5/2012 | Chiba et al. |
| 2012/0132525 | A1 | 5/2012 | Liu et al. |
| 2013/0075276 | A1 | 3/2013 | Hoashi et al. |
| 2013/0130230 | A1 | 5/2013 | Nishizawa et al. |
| 2013/0209807 | A1 | 8/2013 | Chatterjee |
| 2014/0353154 | A1* | 12/2014 | Joshi ................ B82Y 15/00 205/792 |
| 2017/0173036 | A1 | 6/2017 | Alfonta et al. |
| 2017/0191105 | A1 | 7/2017 | Tsugawa et al. |
| 2017/0322167 | A1 | 11/2017 | Swager et al. |
| 2019/0194714 | A1 | 6/2019 | Muguruma et al. |

FOREIGN PATENT DOCUMENTS

| | | |
|---|---|---|
| CN | 101475790 A | 7/2009 |
| CN | 102478539 A | 5/2012 |
| CN | 103018292 A | 4/2013 |
| CN | 103472108 A | 12/2013 |
| JP | 2008-064724 A | 3/2008 |
| JP | 2010-156605 A | 7/2010 |
| JP | 2014-194411 A | 10/2014 |
| JP | 2015-131734 A | 7/2015 |
| WO | WO 2005/088288 A1 | 9/2005 |
| WO | WO 2005/093400 A1 | 10/2005 |
| WO | WO 2005/093888 A2 | 10/2005 |
| WO | WO 2011/007582 A1 | 1/2011 |
| WO | WO 2012/002290 A1 | 1/2012 |
| WO | WO 2017/098076 A1 | 6/2017 |
| WO | WO 2018/043050 A1 | 3/2018 |

OTHER PUBLICATIONS

H. Zhang, et al., "Electrochemical behavior of multi-wall carbon nanotubes and electrocatalysis of toluene-filled nanotube film on gold electrode", Electrochimica Acta, 49(5): p. 715-719, Feb. 2004.*

European Patent Office, Extended European Search Report in European Patent Application No. 19775049.0 (dated Feb. 4, 2022).

Hou et al., "An integrated device of enzymatic biofuel cells and supercapacitor for both efficient electric energy conversion and storage," Electrochimica Acta, 245: 303-308 (2017).

Muguruma et al., "Mediatorless Direct Electron Transfer between Flavin Adenine Dinucleotide-Dependent Glucose Dehydrogenase and Single-Walled Carbon Nanotubes," ACS Catal., 7(1): 725-734 (2017).

Japanese Patent Office, International Search Report in International Patent Application No. PCT/JP2019/014133 (dated Jun. 11, 2019).

Kong et al., "New faces of porous Prussian blue: interfacial assembly of integrated hetero-structures for sensing applications," Chem. Soc. Rev., 44(22): 7997-8018 (2015).

European Patent Office, Communication Pursuant to Rule 164(1) EPC in European Patent Application No. 19775049.0 (dated Nov. 23, 2021).

Fapyane et al., "Immobilisation of Flavin-Adenine-Dinucleotide-Dependent Glucose Dehydrogenase α Subunit in Free-Standing Graphitised Carbon Nanofiber Paper Using a Bifunctional Cross-Linker for an Enzymatic Biofuel Cell," ChemElectroChem, 1(11): 1844-1848 (2014).

Giroud et al., "Anthracene-Modified Pyrenes Immobilized on Carbon Nanotubes for Direct Electroreduction of $O_2$ by Laccase," Electrochemistry Communications, 34: 157-160 (2013).

Haddad et al., "Pyrene-Adamantane-β-Cyclodextrin: An Efficient Host-Guest System for the Biofunctionalization of SWCNT Electrodes," Carbon, 49(7): 2571-2578 (2011).

Japan Patent Office, Office Action in Japanese Patent Application No. 2020-511116 (dated Jul. 4, 2023).

Yin et al., "A Glucose Biosensor Based on Nanomaterials and Paracetamol," Guangdong Chemical Industry, 43(02): 7-8+4 (2016).

China National Intellectual Property Administration, Second Office Action in Chinese Patent Application No. 201980023140.1 (dated Aug. 18, 2023).

\* cited by examiner

ELECTRON TRANSFER BY NANOCARBON

CROSS-REFERENCE TO RELATED APPLICATIONS

This patent application is the U.S. national phase of International Patent Application No. PCT/JP2019/014133, filed on Mar. 29, 2019, which claims the benefit of Japanese Patent Application No. 2018-065464, filed on Mar. 29, 2018, and Japanese Patent Application No. 2019-029534, filed on Feb. 21, 2019, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 35,499 bytes ASCII (Text) file named "750909ReplacementSequenceListing.txt," created Feb. 22, 2021.

TECHNICAL FIELD

Techniques for electron transfer between nanocarbon and other substances are disclosed.

BACKGROUND ART

Nanocarbon, which has a high electrical conductivity, is being increasingly applied as a conductive material for transferring electrons with other substances. For example, it has been proposed to mix nanocarbon with an ink made of carbon, a resin, and an organic solvent, and print it on a substrate for use as an electrode for a biosensor (PTL 1). Further, carbon nanotubes, which are a kind of nanocarbon, are used in sensors for measuring peroxides (PTL 2), or are formed into films together with enzymes and used as electrodes for sensors and fuel cells (PTL 3). Furthermore, it has been reported that electrons are transferred from enzymes to electrodes by direct electron transfer using single-walled carbon nanotubes (NPL 1). This makes it possible to use glucose dehydrogenase (FADGDH) using flavin adenine dinucleotide as a coenzyme, which conventionally requires mediators, in glucose sensors without using mediators.

CITATION LIST

Patent Literature

PTL 1: WO2005088288
PTL 2: WO2011007582
PTL 3: WO2012002290

Non-Patent Literature

NPL 1: ACS Catal. 2017, 7, 725-734

SUMMARY OF INVENTION

Technical Problem

An object of the present invention is to provide a means for promoting electron transfer between nanocarbon and other substances.

Solution to Problem

As a result of intensive studies to achieve the above object, it was found that compounds having an aromatic ring skeleton have an action of promoting the electron transfer function of nanocarbon. Upon further research and improvement based on this finding, the invention represented by the following has been provided.

Item 1.
An electron transfer accelerator for nanocarbon, comprising a compound having an aromatic ring skeleton.

Item 2.
Nanocarbon attached or present in close proximity to a compound having an aromatic ring skeleton due to intermolecular interaction.

Item 3.
The nanocarbon according to Item 2, wherein the compound having an aromatic ring skeleton is a compound that does not function as a mediator by itself.

Item 4.
The nanocarbon according to Item 2 or 3, wherein the compound having an aromatic ring skeleton is selected from the group consisting of thymol, phenol, bis(4-hydroxyphenyl)sulfone, tyrosine disodium hydrate, sodium salicylate, toluene, 5-hydroxyindole, aniline, leucoquinizarin, carvacrol, 1,5-naphthalene diol, 4-isopropyl-3-methylphenol, 2-isopropylphenol, 4-isopropylphenol, 1-naphthol, 2-tert-butyl-5-methylphenol, 2,4,6-trimethylphenol, 2,6-diisopropylphenol, 2-tert-butyl-4-ethylphenol, 6-tert-butyl-2,4-xylenol, 2-tert-butyl-4-methylphenol, 2-tert-butyl-6-methylphenol, 2,4-di-tert-butylphenol, 2,4-di-tert-butyl-5-methylphenol, bis(p-hydroxyphenyl)methane, 3-tert-butylphenol, 2-isopropyl-5-methylanisole, o-cresol, m-cresol, and p-cresol.

Item 5.
An electrode loaded with nanocarbon, a compound having an aromatic ring skeleton, and an enzyme on a substrate.

Item 6.
The electrode according to Item 5, wherein the nanocarbon is a carbon nanotube.

Item 7.
The electrode according to Item 5 or 6, wherein the carbon nanotube is a single-walled carbon nanotube.

Item 8.
The electrode according to any one of Items 5 to 7, wherein the enzyme is flavin-binding glucose dehydrogenase.

Item 9.
The electrode according to any one of Items 5 to 8, further comprising a dispersant loaded on the substrate.

Item 10.
The electrode according to any one of Items 5 to 9, wherein a thin film of carbon or metal is formed on the substrate.

Item 11.
A sensor comprising the electrode according to any one of Items 5 to 10.

Item 12.
Use of a compound having an aromatic ring skeleton for promoting or improving electron transfer by nanocarbon.

Item 13.
The use according to Item 12, wherein the electron transfer by nanocarbon is electron transfer between an electrode and an enzyme.

Item 14.
The use according to Item 13, wherein the enzyme is flavin-binding glucose dehydrogenase.

Item 15.
The use according to any one of Items 12 to 14, wherein the compound having an aromatic ring skeleton is selected from the group consisting of thymol, phenol, bis(4-hydroxyphenyl)sulfone, tyrosine disodium hydrate, sodium salicylate, toluene, 5-hydroxyindole, aniline, leucoquinizarin, carvacrol, 1,5-naphthalene diol, 4-isopropyl-3-methylphenol, 2-isopropylphenol, 4-isopropylphenol, 1-naphthol, 2-tert-butyl-5-methylphenol, 2,4,6-trimethylphenol, 2,6-diisopropylphenol, 2-tert-butyl-4-ethylphenol, 6-tert-butyl-2,4-xylenol, 2-tert-butyl-4-methylphenol, 2-tert-butyl-6-methylphenol, 2,4-di-tert-butylphenol, 2,4-di-tert-butyl-5-methylphenol, bis(p-hydroxyphenyl)methane, 3-tert-butylphenol, 2-isopropyl-5-methylanisole, o-cresol, m-cresol, and p-cresol.

Item 16.

The use according to any one of Items 12 to 15, wherein the nanocarbon is a carbon nanotube.

Item 17.

A method for promoting or improving electron transfer by nanocarbon, the method comprising attaching or bringing close a compound having an aromatic ring skeleton to nanocarbon.

Item 18.

The method according to Item 17, wherein the electron transfer by nanocarbon is electron transfer between an electrode and an enzyme.

Item 19.

The method according to Item 18, wherein the enzyme is flavin-binding glucose dehydrogenase.

Item 20.

The method according to any one of Items 17 to 19, wherein the compound having an aromatic ring skeleton is attached or brought close to nanocarbon by loading the nanocarbon, the compound having an aromatic ring skeleton, and an enzyme on an electrode substrate.

Item 21.

The method according to any one of Items 17 to 19, wherein the compound having an aromatic ring skeleton is attached or brought close to nanocarbon by immersing an electrode loaded with the nanocarbon and an enzyme on a substrate in a solvent containing the compound having an aromatic ring skeleton.

Item 22.

The method according to Item 21, wherein the concentration of the compound having an aromatic ring skeleton in the solvent is 0.000001 to 2% (w/v).

Item 23.

The method according to any one of Items 17 to 22, wherein the compound having an aromatic ring skeleton is selected from the group consisting of thymol, phenol, bis(4-hydroxyphenyl)sulfone, tyrosine disodium hydrate, sodium salicylate, toluene, 5-hydroxyindole, aniline, leucoquinizarin, carvacrol, 1,5-naphthalene diol, 4-isopropyl-3-methylphenol, 2-isopropylphenol, 4-isopropylphenol, 1-naphthol, 2-tert-butyl-5-methylphenol, 2,4,6-trimethylphenol, 2,6-diisopropylphenol, 2-tert-butyl-4-ethylphenol, 6-tert-butyl-2,4-xylenol, 2-tert-butyl-4-methylphenol, 2-tert-butyl-6-methylphenol, 2,4-di-tert-butylphenol, 2,4-di-tert-butyl-5-methylphenol, bis(p-hydroxyphenyl)methane, 3-tert-butylphenol, 2-isopropyl-5-methylanisole, o-cresol, m-cresol, and p-cresol.

Item 24.

The method according to any one of Items 17 to 23, wherein the nanocarbon is a carbon nanotube.

Item 25.

A sensor comprising an electrode immersed in a solvent containing a compound having an aromatic ring skeleton, wherein the electrode is loaded with nanocarbon and an enzyme on a substrate.

Item 26.

The sensor according to Item 25, wherein the concentration of the compound having an aromatic ring skeleton in the solvent is 0.000001 to 2% (w/v).

Advantageous Effects of Invention

Electron transfer by nanocarbon is promoted. Therefore, the field of application of electron transfer by nanocarbon will be expanded. In one embodiment, nanocarbon can be stably and/or more effectively used as a mediator of electron transfer between enzymes and electrodes.

DESCRIPTION OF EMBODIMENTS

1. Electron Transfer Accelerator for Nanocarbon

Figure 1:
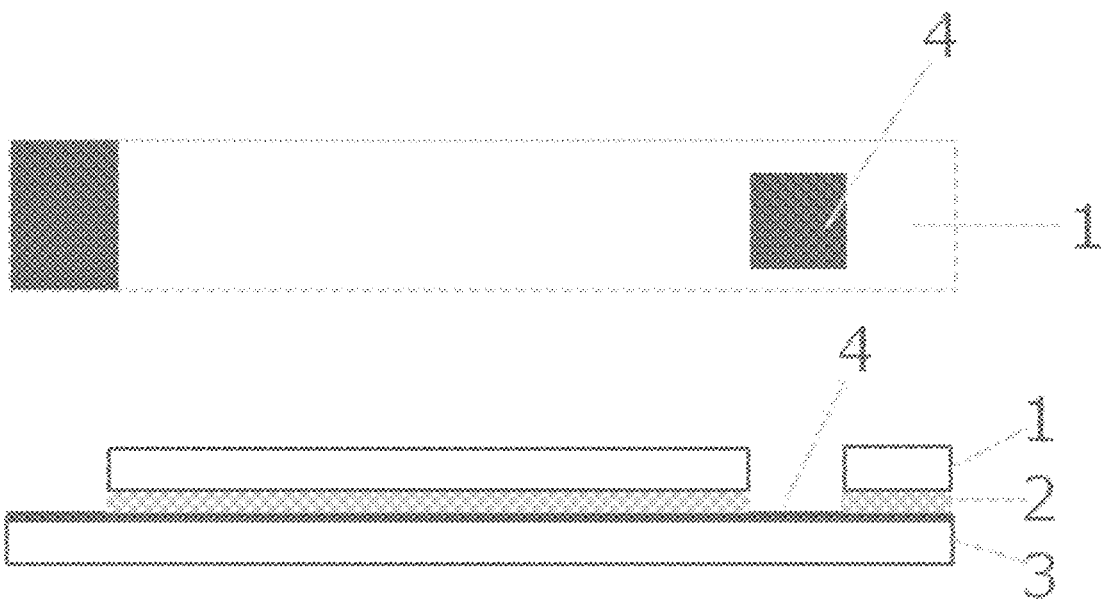
FIG. 1 shows the structure of an electrode produced in Example 1. "1" denotes a PET film, "2" denotes an adhesive sheet, "3" denotes a gold-deposited PET film, and "4" denotes a working electrode section.

The nanocarbon is not particularly limited as long as it is a substance that has an electron transfer function and that is recognized as nanocarbon. Examples of such substances include carbon materials mainly composed of carbon, including carbon nanotubes, carbon nanohorns, carbon nanotwists, cocoons, carbon nanocoils, graphene, and fullerene. The carbon nanotubes may be single-walled carbon nanotubes, double-walled carbon nanotubes, or multi-walled carbon nanotubes. In one embodiment, the nanocarbon is preferably carbon nanotubes, and more preferably single-walled carbon nanotubes.

The electron transfer accelerator for nanocarbon preferably comprises a compound having an aromatic ring skeleton. The number of ring-forming atoms in the aromatic ring skeleton is, for example, 5 to 18, preferably 5 to 16, and more preferably 5 to 14. Examples of the aromatic ring skeleton include a skeleton composed of one benzene ring, a skeleton composed of two or more (e.g., 2 to 4) benzene rings (naphthalene skeleton, anthracene skeleton, etc.), a skeleton composed of a condensed ring of a benzene ring and another aromatic ring (e.g., nitrogen-containing aromatic ring, oxygen-containing aromatic ring, or sulfur-containing aromatic ring) (phenanthroline skeleton, benzofuran skeleton, benzimidazole skeleton, carbazole skeleton, etc.), and a skeleton composed of an aromatic ring composed of carbon and another element (e.g., nitrogen, oxygen, or sulfur) (triazine skeleton, triazole skeleton, pyridine skeleton, etc.). The compound having an aromatic ring skeleton is preferably a compound that does not function as a mediator by itself. The compound "that does not function as a mediator by itself" means that it does not have the function of transferring electrons by itself between electrodes and enzymes or between electrodes and substrates, unlike benzoquinone and 1-methoxyphenazine methosulfate.

In one embodiment, the compound having an aromatic ring skeleton preferably has an electron-donating substituent. The electron-donating substituent refers to a hydroxy group, an amino group, a methyl group, or the like. The electron-donating substituent is preferably a hydroxy group. Examples of compounds having an electron-donating substituent and an aromatic ring skeleton include compounds having a benzene ring substituted with a hydroxy group (e.g., thymol, phenol, bis(4-hydroxyphenyl)sulfone, tyrosine disodium hydrate, sodium salicylate, 5-hydroxyindole, leucoquinizarin, carvacrol, 1,5-naphthalene diol, 4-isopropyl-3-methylphenol, 2-isopropylphenol, 4-isopropylphenol, 1-naphthol, 2-tert-butyl-5-methylphenol, 2,4,6-trimethylphenol, 2,6-diisopropylphenol, 2-tert-butyl-4-ethylphenol, 6-tert-butyl-2,4-xylenol, 2-tert-butyl-4-methylphenol, 2-tert-butyl-6-methylphenol, 2,4-di-tert-butylphenol, 2,4-di-tert-butyl-5-methylphenol, bis(p-hydroxyphenyl)methane, 3-tert-butylphenol, o-cresol, m-cresol, and p-cresol), compounds having a benzene ring substituted with an amino group (e.g., aniline), and compounds having a benzene ring substituted with a methyl group (e.g., toluene and 2-isopropyl-5-methylanisole).

Among the above compounds, thymol, phenol, and carvacrol are preferable.

When the electron transfer accelerator for nanocarbon is brought close to or attached to nanocarbon, the electron transfer between the nanocarbon and other substances can be promoted. It is preferable that the electron transfer accelerator and nanocarbon are attached or close to each other due to intermolecular interaction. The amount of electron transfer accelerator arranged close to or attached to nanocarbon to promote the electron transfer by nanocarbon is not particularly limited.

2. Nanocarbon to Which Electron Transfer Accelerator Is Close or Attached

When the electron transfer accelerator is brought close to or attached to nanocarbon, the electron transfer by the resulting nanocarbon can be promoted. The means for bringing close or attaching the electron transfer accelerator to nanocarbon is not particularly limited. For example, it can be achieved by mixing nanocarbon and the electron transfer accelerator (including mixing them in a solution), or by arranging the electron transfer accelerator on nanocarbon. The electron transfer accelerator arranged close to or attached to nanocarbon may or may not be immobilized. The immobilization is not limited as long as it does not impair the functions of the nanocarbon and the electron transfer accelerator, and can be suitably selected from known means and used.

The nanocarbon and electron transfer accelerator that can be used in the nanocarbon to which the electron transfer accelerator is close or attached are as described in section 1 above.

3. Electrode

The electrode preferably has a substrate on which nanocarbon, a compound having an aromatic ring skeleton, and an enzyme are loaded. The nanocarbon and the compound having an aromatic ring skeleton are as described in section 1 above.

The amount of the compound having an aromatic ring skeleton loaded is not particularly limited. The amount of the compound having an aromatic ring skeleton loaded is, for example, 0.001 parts by mass or more, preferably 0.01 parts by mass or more, and more preferably 0.1 parts by mass or more, per 100 parts by mass of the amount of nanocarbon loaded. Further, the amount of the compound having an aromatic ring skeleton loaded is, for example, 100000 parts by mass or less, preferably 10000 parts by mass or less, and more preferably 1000 parts by mass or less, per 100 parts by mass of the amount of nanocarbon loaded. The lower limit and the upper limit can be combined in any way. Moreover, the amount of the compound having an aromatic ring skeleton loaded is, for example, 0.001 parts by mass or more, preferably 0.01 parts by mass or more, and more preferably 0.1 parts by mass or more, per 100 parts by mass of the amount of the enzyme loaded. Further, the amount of the compound having an aromatic ring skeleton loaded is, for example, 1000000 parts by mass or less, preferably 100000 parts by mass or less, and more preferably 10000 parts by mass or less, per 100 parts by mass of the amount of the enzyme loaded. The lower limit and the upper limit can be combined in any way.

The substrate is not particularly limited as long as it is suitable for the electrode on which the enzyme used in the biosensor is immobilized. For example, the substrate may be an insulating substrate on which a metal film (e.g., a metal thin film) is formed. The insulating substrate may be, for example, a glass substrate or a plastic substrate (e.g., a PET substrate). The type of metal forming the metal film is not particularly limited as long as it can be used for electrodes. For example, gold, platinum, titanium, etc., can be used. Further, the substrate may have a carbon film (e.g., a thin film of carbon paste), in place of a metal film.

The enzyme is preferably one that releases electrons upon catalytic reaction. Examples of such enzymes include oxidoreductases. Examples of oxidoreductases include glucose dehydrogenase, glucose oxidase, lactate oxidase, cholesterol oxidase, alcohol oxidase, sarcosine oxidase, fructosylamine oxidase, pyruvate oxidase, lactate dehydrogenase, alcohol dehydrogenase, glycerol oxidase, glycerol-3-phosphate oxidase, uricase, choline oxidase, xanthine oxidase, hydroxybutyrate dehydrogenase, and the like.

In one embodiment, the enzyme is preferably glucose dehydrogenase, more preferably flavin-binding glucose dehydrogenase, and even more preferably glucose dehydrogenase using flavin adenine dinucleotide (FAD) as a coenzyme (also referred to as "FADGDH"). Since FADGDH retains FAD in recesses of the three-dimensional structure formed by polypeptides, a substance called a mediator has been conventionally required to transfer electrons generated therein to electrodes. In contrast, the use of nanocarbon (preferably carbon nanotubes, and more preferably single-walled carbon nanotubes) makes it possible to transfer electrons to electrodes without using a mediator. Further, the use of the electron transfer accelerator described above makes it possible to perform electron transfer via nanocarbon significantly efficiently (or strongly).

The type of FADGDH is not limited, and any type can be used. Specific examples of FADGDH include those derived from any of the following organisms: *Aspergillus terreus*, *Aspergillus oryzae*, *Aspergillus niger*, *Aspergillus foetidus*, *Aspergillus aureus*, *Aspergillus versicolor*, *Aspergillus kawachii*, *Aspergillus awamori*, *Agrobacterium tumefaciens*, *Cytophaga marinoflava*, *Agaricus bisporus*, *Macrolepiota rhacodes*, *Burkholderia cepacia*, *Mucor subtilissimus*, *Mucor guilliermondii*, *Mucor prainii*, *Mucor javanicus*, *Mucor circinelloides*, *Mucor circinelloides* f. *circinelloides*, *Mucor hiemalis*, *Mucor hiemalis* f. *silvaticus*, *Mucor dimorphosporus*, *Absidia cylindrospora*, *Absidia hyalospora*, *Actinomucor elegans*, *Circinella simplex*, *Circinella angarensis*, *Circinella chinensis*, *Circinella lacrymispora*, *Circinella minor*, *Circinella mucoroides*, *Circinella rigida*, *Circinella umbellata*, *Circinella muscae*, *Metarhizium* sp., and *Colletotrichum* sp.

In one embodiment, the FADGDH is preferably FADGDH derived from *Aspergillus oryzae*, FADGDH derived from *Mucor hiemalis*, FADGDH derived from *Mucor* subtilissimus, FADGDH derived from *Circinella simplex*, FADGDH derived from *Metarhizium* sp., or FADGDH derived from *Colletotrichum* sp. The FADGDH preferably has 80% or more, more preferably 90% or more, and even more preferably 95% or more, identity to the amino acid sequences of SEQ ID Nos. 1 to 6. FADGDH having glucose dehydrogenation activity can be used. The amino acid sequence identity can be calculated using an analysis tool that is commercially available or available through a telecommunication line (the internet). For example, the amino acid sequence identity can be calculated using the homology algorithm BLAST (Basic Local Alignment Search Tool) of the National Center for Biotechnology Information (NCBI) (http://www.ncbi.nlm.nih.gov/BLAST/) with default (initially set) parameters. SEQ ID No. 1 is the amino acid sequence of FADGDH derived from *Aspergillus oryzae*, SEQ ID No. 2 is the amino acid sequence of FADGDH derived from *Mucor hiemalis*, SEQ ID No. 3 is the amino acid sequence of FADGDH derived from *Mucor* subtilissimus, SEQ ID No. 4 is the amino acid sequence of FADGDH derived from *Circinella simplex*, SEQ ID No. 5 is the amino acid sequence of FADGDH derived from *Metarhizium* sp., and SEQ ID No. 6 is the amino acid sequence of FADGDH derived from *Colletotrichum* sp.

A dispersant may be further loaded on the substrate. The dispersant is not particularly limited as long as it is a substance capable of suppressing the aggregation of nanocarbon on the substrate and dispersing it. Examples of the dispersant include sodium cholate, sodium deoxycholate, sodium dodecylsulfate, sodium dodecylbenzenesulfonate, cetyltrimethylammonium bromide, octylphenol ethoxylate, and the like. In one embodiment, the dispersant is preferably sodium cholate or sodium deoxycholate.

The nanocarbon, the compound having an aromatic ring skeleton, and the enzyme can be loaded on the substrate by any means. For example, solutions in which these substances are each dispersed or dissolved are prepared, and these solutions are sequentially added dropwise to a predetermined portion on the substrate (when the substrate is an insulating substrate on which a metal thin film is formed, the portion where the metal thin film is formed) and dried; this operation can be repeated to load them. The dispersion medium or solvent is not particularly limited, and examples thereof include water, alcohol solvents (e.g., ethanol), ketone solvents (e.g., acetone), and combinations thereof.

They may be loaded in any order; however, in one embodiment, the order of loading is preferably nanocarbon←enzyme←compound having an aromatic ring skeleton, or compound having an aromatic ring skeleton←nanocarbon←enzyme.

The amounts of nanocarbon, compound having an aromatic ring skeleton, and enzyme used are not particularly limited.

In one embodiment, the nanocarbon, the compound having an aromatic ring skeleton, and the enzyme may be immobilized on the substrate. Immobilization can be performed by suitably selecting a known method. For example, immobilization can be performed in such a manner that a liquid in which substances suitable for immobilization, such as a tetrafluoroethylene/perfluoro [2-(fluorosulfonylethoxy) polyvinyl ether] copolymer (e.g., Nafion (trademark)) and carboxymethyl cellulose, are dissolved is added dropwise to the substrate in a portion in which each of the above substances is loaded, followed by drying. In one embodiment, it is preferable that the nanocarbon, the compound having an aromatic ring skeleton, and the enzyme are loaded on the substrate, followed by treatment with a polymer substance, such as carboxymethyl cellulose, so as to cover these substances.

In one embodiment, the dispersant is preferably mixed with a dispersion in which nanocarbon is dispersed. The mixing ratio of the dispersant is any ratio, and is preferably 0.2 to 2% (w/v), for example. The mixing ratio of the nanocarbon is also any ratio, and is preferably 0.05 to 0.5% (w/v), for example.

4. Sensor

The sensor preferably comprises the electrode described in section 3 above. In one embodiment, the sensor preferably comprises the electrode of section 3 as a working electrode. The sensor preferably has a counter electrode, in addition to the working electrode. The sensor may further comprise configurations that are generally found in biosensors, such as a potentiostat and a current-sensing circuit. The counter electrode, potentiostat, current-sensing circuit, etc., may specifically have any configurations as long as the intended measurement can be performed by the sensor, and the specific configurations can be suitably selected from means known in the art and designed.

In one embodiment, the working electrode included in the sensor may be an electrode obtained by removing the compound having an aromatic ring skeleton from the electrode of section 3. When such a working electrode is used, it is preferable that the solvent (containing a substance to be measured or a substrate) in which each electrode is immersed contains a compound having an aromatic ring skeleton. Typical examples of solvents include buffers, and examples thereof include acetate buffers, citrate buffers, phosphate buffers, borate buffers, and the like.

The concentration of the substance to be measured or the substrate in the solvent is not particularly limited, and can be set to any concentration necessary for measurement.

The concentration of the compound having an aromatic ring skeleton in the solvent is not particularly limited. The lower limit of the concentration is, for example, 0.000001% (w/v), preferably 0.000005% (w/v), more preferably 0.00001% (w/v), more preferably 0.00005% (w/v), more preferably 0.0001% (w/v), more preferably 0.0005% (w/v), more preferably 0.001% (w/v), more preferably 0.005% (w/v), and more preferably 0.01% (w/v). The upper limit of the concentration is, for example, 2% (w/v), preferably 1.5% (w/v), and more preferably 1% (w/v). The lower limit and upper limit of the concentration can be combined in any way.

These sensors can be used to detect and measure targets.

EXAMPLES

The present invention is described in more detail below with reference to Examples; however, the present invention is not limited thereto.

Example 1

An electrode tip having a 9 mm² working electrode section was produced using a sheet obtained by depositing gold on a PET substrate (FIG. 1). In FIG. 1, "1" denotes a PET film, "2" denotes an adhesive sheet, "3" denotes a gold-deposited PET film, and "4" denotes a working electrode section. To the working electrode section, 5 μL of a water dispersion containing 2% (w/v) sodium cholate and 0.15% (w/v) single-walled carbon nanotubes (SuperPureTubes, NanoIntegris, outer diameter: 1.1 to 1.7 nm) was added dropwise and dried. After drying the carbon nanotube dispersion, 5 μL of FADGDH (having the amino acid sequence of SEQ ID No. 2; 20 U/μL) dissolved in ultrapure water was added dropwise to the working electrode section and dried. After drying the FADGDH liquid, 5 μL of the following compound (1) or (2) (each 1% (w/v) solution) was added dropwise to the working electrode section and dried.
(1) thymol (dissolved in 50% (v/v) ethanol)
(2) phenol (dissolved in a 40 mM sodium phosphate buffer)

After drying the compound liquid, 5 μL of 3% (w/v) Nafion liquid was added dropwise to the working electrode section and dried to immobilize the carbon nanotubes and FAD-GDH on the working electrode. The electrode tip produced above was set as the working electrode of an electrochemical analyzer (ALS/CHI 660B, produced by ABS Inc.), a silver/silver chloride electrode was set as the reference electrode, and a platinum wire was set as the counter electrode. These three electrodes were immersed in a 40 mM sodium phosphate buffer (pH 7.4). Cyclic voltammetry measurement was performed when glucose was not added to this buffer (0 mM), or when glucose was added at 10 mM or 48 mM.

Figure 2:
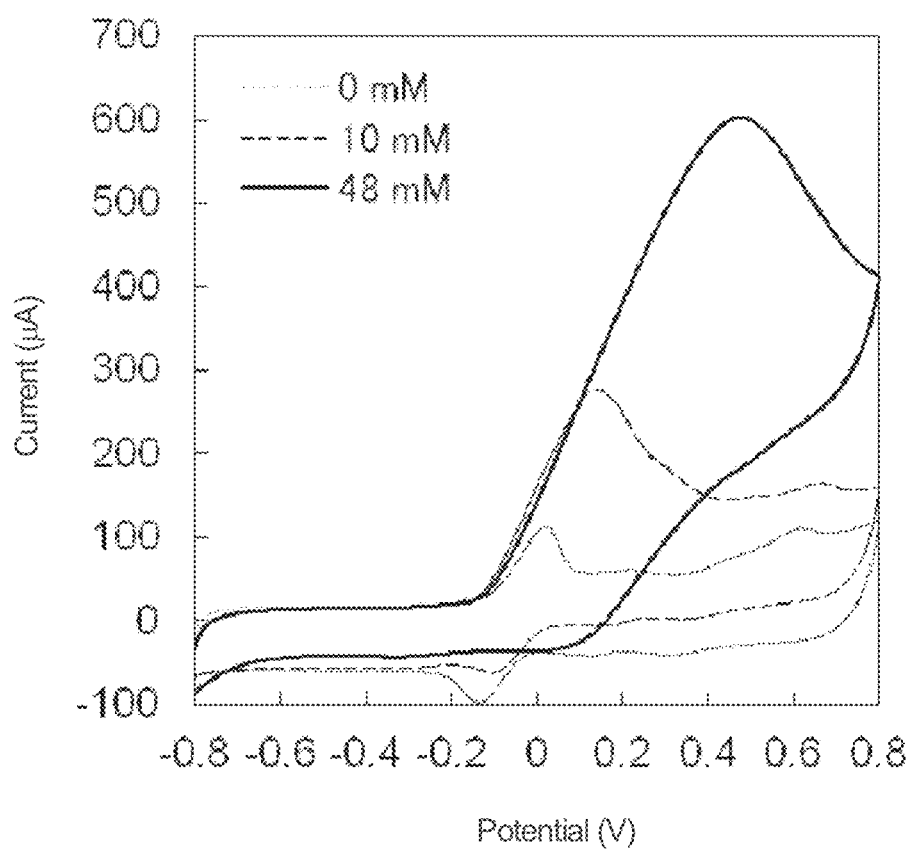
FIG. 2 shows cyclic voltammograms measured while loading thymol on the working electrode section in Example 1.
Figure 3:
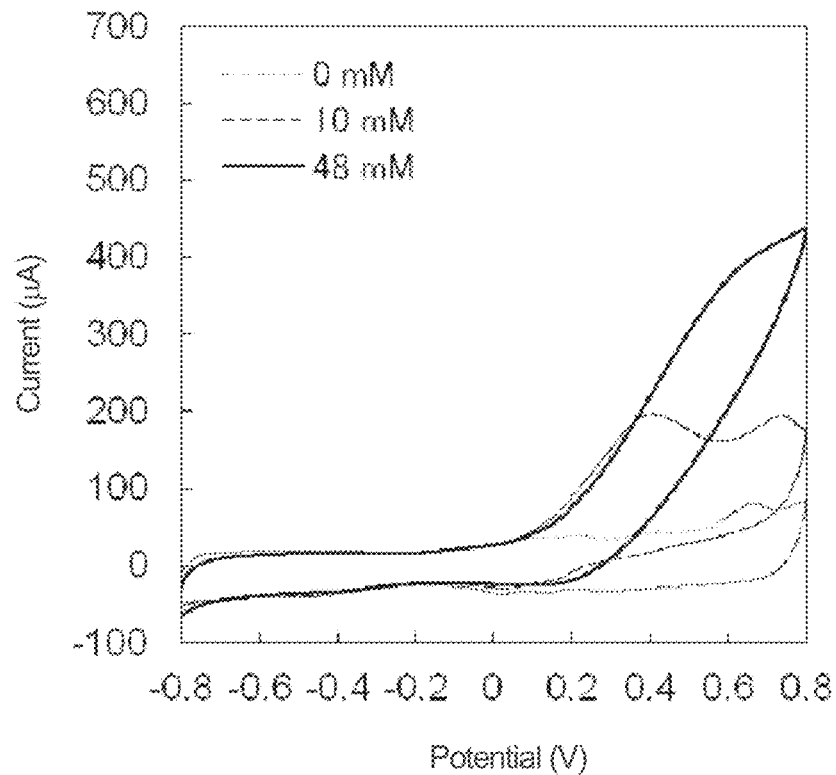
FIG. 3 shows cyclic voltammograms measured while loading phenol on the working electrode section in Example 1.

FIGS. 2 and 3 show the cyclic voltammograms measured at glucose concentrations of 0 mM, 10 mM, and 48 mM. FIG. 2 shows the case of using thymol, and FIG. 3 shows the case of using phenol.

In the cyclic voltammograms, the current values at +0.6 V when sweeping from −0.8 V to +0.8 V are as shown in Table 1 below.

TABLE 1

| | Current value (μA) | | |
|---|---|---|---|
| Compound added | (a) 0 mM glucose | (b) 48 mM glucose | (b)-(a) |
| (1) Thymol | 108 | 539 | 431 |
| (2) Phenol | 63 | 373 | 309 |

Comparative Example 1

Cyclic voltammograms were measured in the same manner as in Example 1, except that compound (1) of Example 1 was changed to the following compound (3) or (4).
(3) menthol (dissolved in 50% (v/v) ethanol)
(4) cyclohexanol (dissolved in a 40 mM sodium phosphate buffer)

Figure 4:
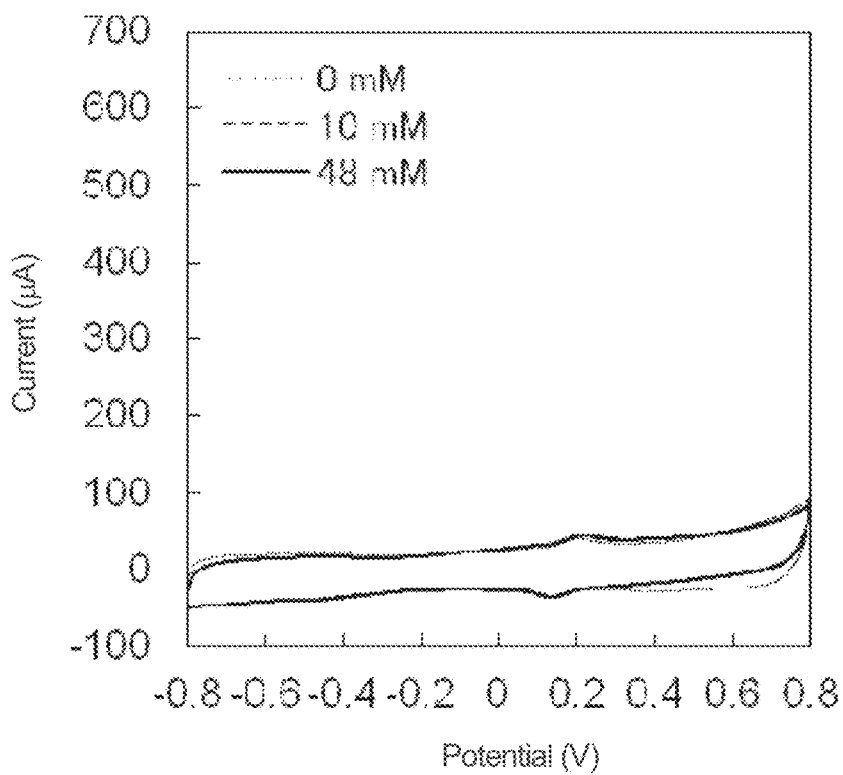
FIG. 4 shows cyclic voltammograms measured while loading menthol on the working electrode section in Comparative Example 1.
Figure 5:
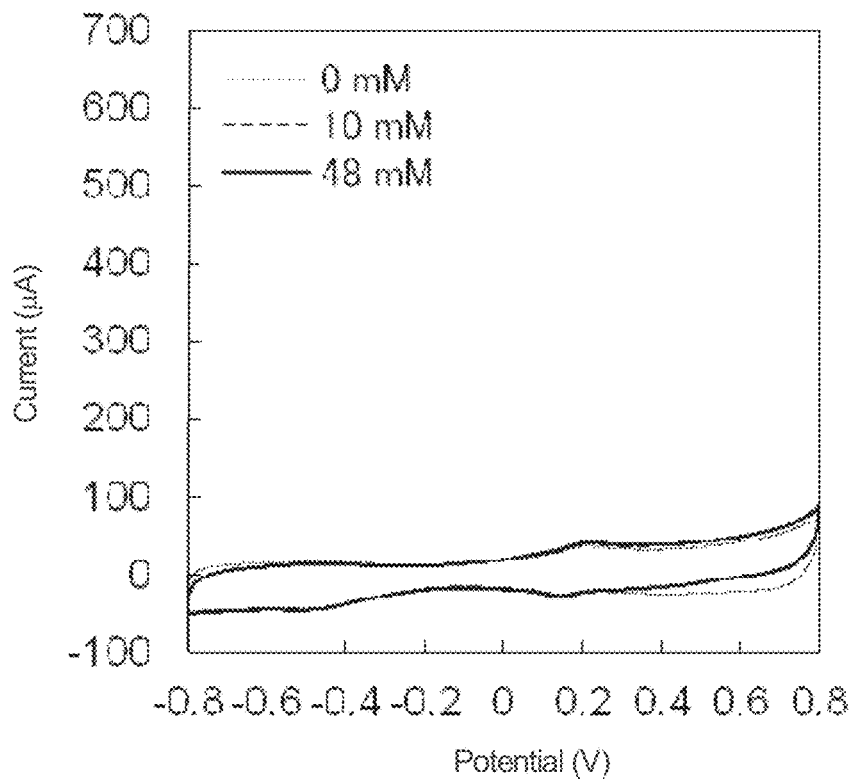
FIG. 5 shows cyclic voltammograms measured while loading cyclohexanol on the working electrode section in Comparative Example 1.
Figure 6:
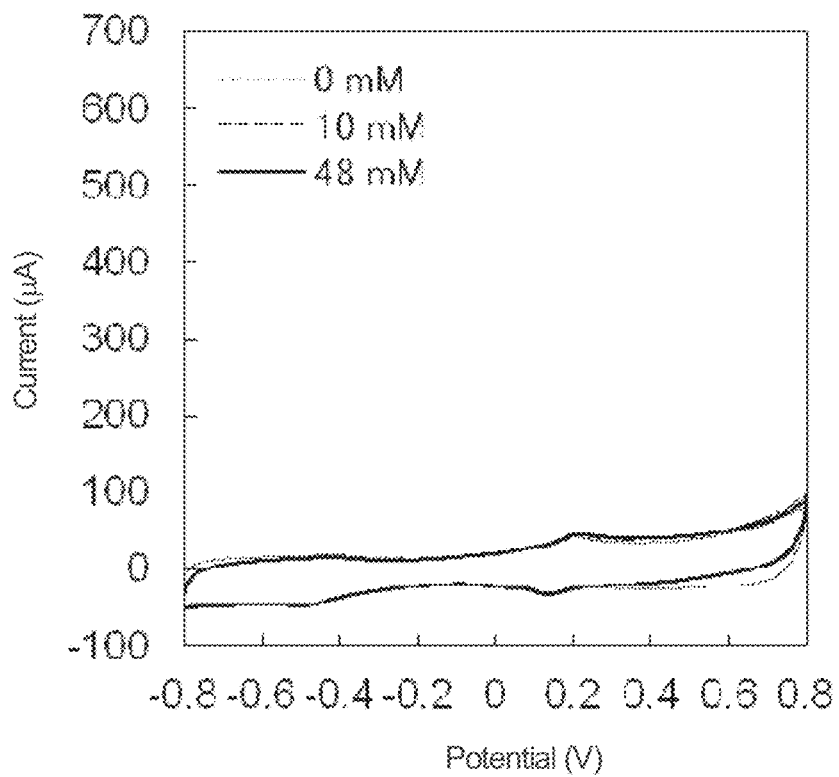
FIG. 6 shows cyclic voltammograms measured without loading a compound on the working electrode section in Comparative Example 1.

The results are shown in FIG. 4 (menthol), FIG. 5 (cyclohexanol), and FIG. 6 (no compound added). In the cyclic voltammograms shown in FIGS. 4 to 6, the current values at +0.6 V when sweeping from −0.8 V to +0.8 V were as shown in Table 2 below.

TABLE 2

| | Current value (μA) | | |
|---|---|---|---|
| Compound added | (a) 0 mM glucose | (b) 48 mM glucose | (b)-(a) |
| (3) Menthol | 47 | 50 | 3 |
| (4) Cyclohexanol | 42 | 49 | 7 |
| Not added | 46 | 51 | 5 |

The results of Example 1 and Comparative Example 1 revealed that the current could be measured by adding thymol or phenol even under the conditions in which the current could not be measured only by immobilizing the enzyme and carbon nanotubes on the working electrode section. On the other hand, it was revealed that the current was not measured when menthol or cyclohexanol was used instead of thymol and phenol.

Example 2

An electrode tip having a 9 mm² working electrode section was produced using a sheet obtained by depositing gold on a PET substrate, in the same manner as in Example 1. To the working electrode section, 5 μL of a water dispersion containing 2% (w/v) sodium cholate and 0.15% (w/v) single-walled carbon nanotubes (outer diameter: 1.1 to 1.7 nm) was added dropwise and dried. After drying the carbon nanotube dispersion, 5 μL of FADGDH (having the amino acid sequence of SEQ ID No. 2; 20 U/μL) dissolved in ultrapure water was added dropwise to the working electrode section and dried. After drying the FADGDH liquid, 5 μL of 3% (w/v) Nafion liquid was added dropwise to the working electrode section and dried to immobilize the carbon nanotubes and FADGDH on the working electrode.

Then, 0.1% (w/v) of any of the following compounds (5) to (10) was added and dissolved in a 40 mM sodium phosphate buffer (pH 7.4).

(5) phenol (6) bis(4-hydroxyphenyl) sulfone (7) tyrosine disodium hydrate (8) sodium salicylate (9) toluene

(10) 5-hydroxyindole

The electrode produced above was set as the working electrode of an electrochemical analyzer (ALS/CHI 660B), a silver/silver chloride electrode was set as the reference electrode, and a platinum wire was set as the counter electrode. These electrodes were immersed in a sodium phosphate buffer in which any of compounds (5) to (10) above was dissolved. Cyclic voltammetry measurement was performed when glucose was not added to this buffer (0 mM), or when glucose was added at 10 mM or 48 mM. In the obtained cyclic voltammograms, the current values at +0.6 V when sweeping from −0.8 V to +0.8 V were as shown in Table 3 below.

TABLE 3

| Compound added | Current value (A) | | |
|---|---|---|---|
| | (a) 0 mM glucose | (b) 48 mM glucose | (b)-(a) |
| (5) Phenol | 183 | 552 | 369 |
| (6) Bis(4-hydroxyphenyl)sulfone | 72 | 161 | 89 |
| (7) Tyrosine disodium hydrate | 141 | 231 | 90 |
| (8) Sodium salicylate | 81 | 125 | 44 |
| (9) Toluene | 68 | 88 | 20 |
| (10) 5-Hydroxyindole | 675 | 856 | 181 |

As described above, it was confirmed that the current measured in Example 1 was also observed even when thymol or phenol was changed to compounds (5) to (10) above.

Comparative Example 2

Cyclic voltammograms were obtained in the same manner as in Example 2, except that any of compounds (5) to (10) was replaced with compound (3) or (4). In the obtained cyclic voltammograms, the current values at +0.6 V when sweeping from −0.8 V to +0.8 V were as shown in Table 4 below.

TABLE 4

| Compound added | Current value (μA) | | |
|---|---|---|---|
| | (a) 0 mM glucose | (b) 48 mM glucose | (b)-(a) |
| (3) Menthol | 43 | 45 | 2 |
| (4) Cyclohexanol | 40 | 47 | 7 |
| Not added | 41 | 48 | 7 |

As described above, it was confirmed that in the configuration of Example 2, the current was not substantially measured when compounds (5) to (10) were not added or were replaced with menthol or cyclohexanol.

Compounds (1), (2), and (5) to (10) all have an aromatic ring skeleton, whereas compounds (3) and (4) do not have an aromatic ring skeleton. Therefore, it is presumed that due to the aromatic ring skeleton, compounds (1), (2), and (5) to (10) mediate and promote electron transfer between the coenzyme FAD and the carbon nanotubes.

Example 3

Figure 7:
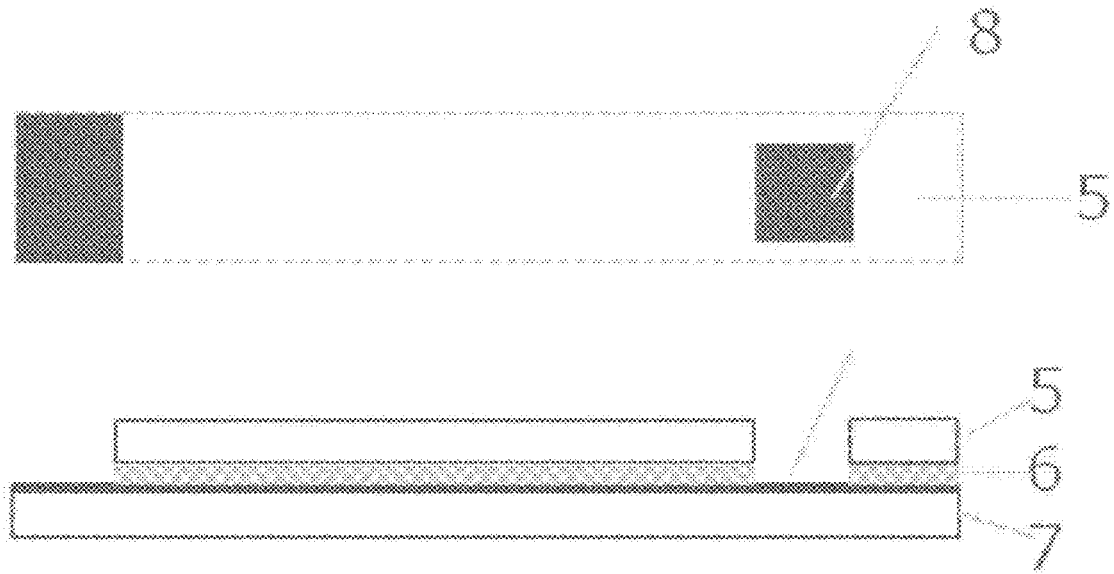
FIG. 7 shows the structure of an electrode produced in Example 3. "5" denotes a PET film, "6" denotes an adhesive sheet, "7" denotes a carbon paste-printed PET film, and "8" denotes a working electrode section.

An electrode tip having a 9 mm$^2$ working electrode section was produced using a sheet obtained by printing carbon paste on a PET substrate (FIG. 7). In FIG. 7, "5" denotes a PET film, "6" denotes an adhesive sheet, "7" denotes a carbon paste-printed PET film, and "8" denotes a working electrode section. To the working electrode section, 5 μL of a water dispersion containing 2% (w/v) sodium cholate and 0.15% (w/v) single-walled carbon nanotubes (outer diameter: 1.1 to 1.7 nm) was added dropwise and dried. After drying the carbon nanotube dispersion, 5 μL of FADGDH (having the amino acid sequence represented by SEQ ID No. 2; 20 U/μL) dissolved in ultrapure water was added dropwise to the working electrode section and dried. After drying the FADGDH liquid, 5 μL of 1% (w/v) carboxymethylcellulose liquid was added dropwise to the working electrode section and dried to immobilize the carbon nanotubes and FAD-GDH on the working electrode. A 5% (w/v) thymol solution dissolved in 50% (v/v) ethanol was added and mixed with a 40 mM sodium phosphate buffer (pH 7.4) to 0.1% (w/v) thymol.

Figure 8:
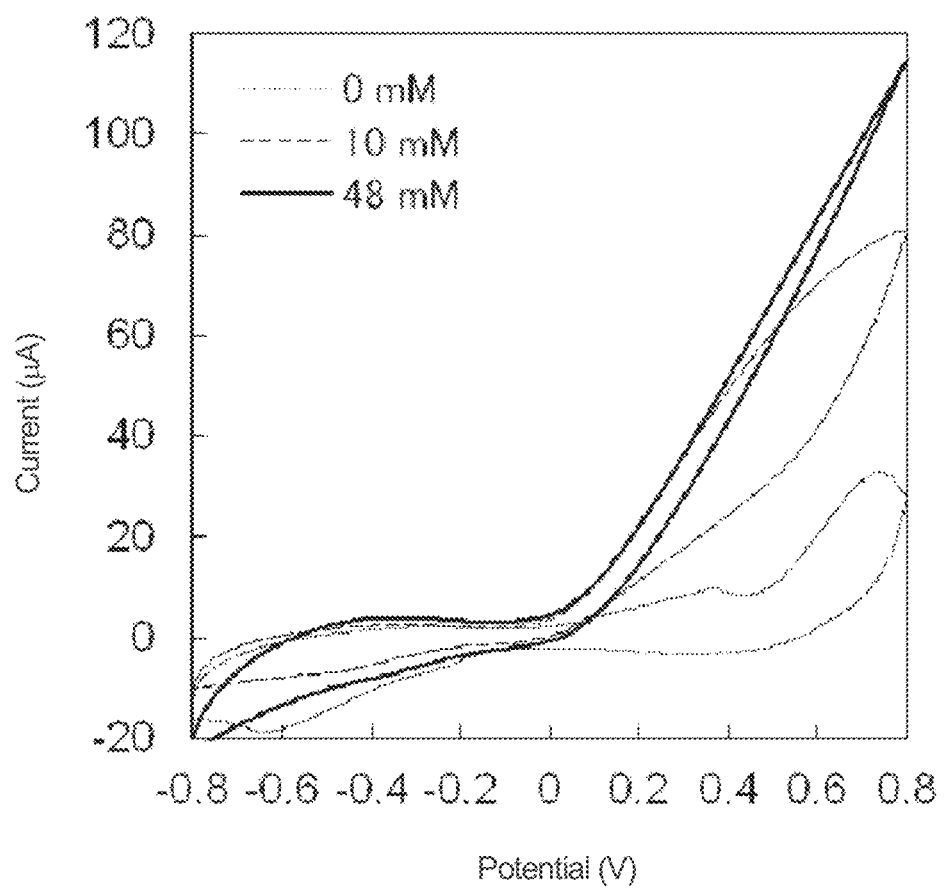
FIG. 8 shows cyclic voltammograms measured while adding thymol to a buffer in Example 3.

The electrode produced above was set as the working electrode of an electrochemical analyzer (ALS/CHI 660B), a silver/silver chloride electrode was set as the reference electrode, and a platinum wire was set as the counter electrode. These electrodes were immersed in a sodium phosphate buffer containing 0.01% (w/v) thymol. Cyclic voltammetry measurement was performed when glucose was not added to this buffer (0 mM), or when glucose was added at 10 mM or 48 mM. FIG. 8 shows the obtained cyclic voltammograms. In the cyclic voltammograms, the current values at +0.6 V when sweeping from −0.8 V to +0.8 V were as shown in Table 5 below.

TABLE 5

| Compound added | Current value (μA) | | |
|---|---|---|---|
| | (a) 0 mM glucose | (b) 48 mM glucose | (b)-(a) |
| Thymol | 20 | 83 | 63 |

Comparative Example 3

Figure 9:
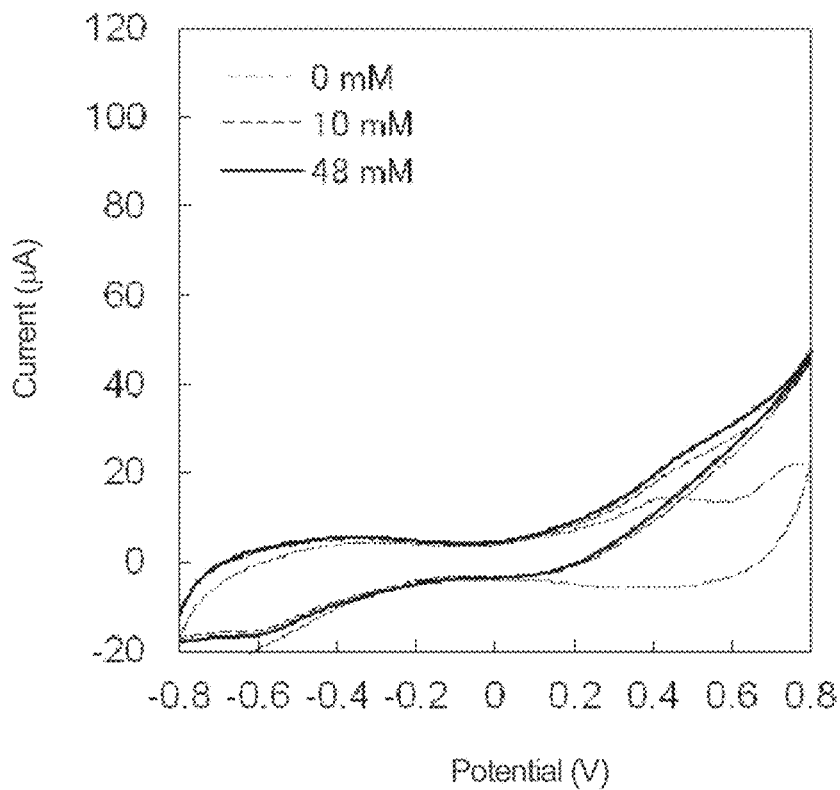
FIG. 9 shows cyclic voltammograms measured without adding thymol to a buffer in Comparative Example 3.
Figure 10:
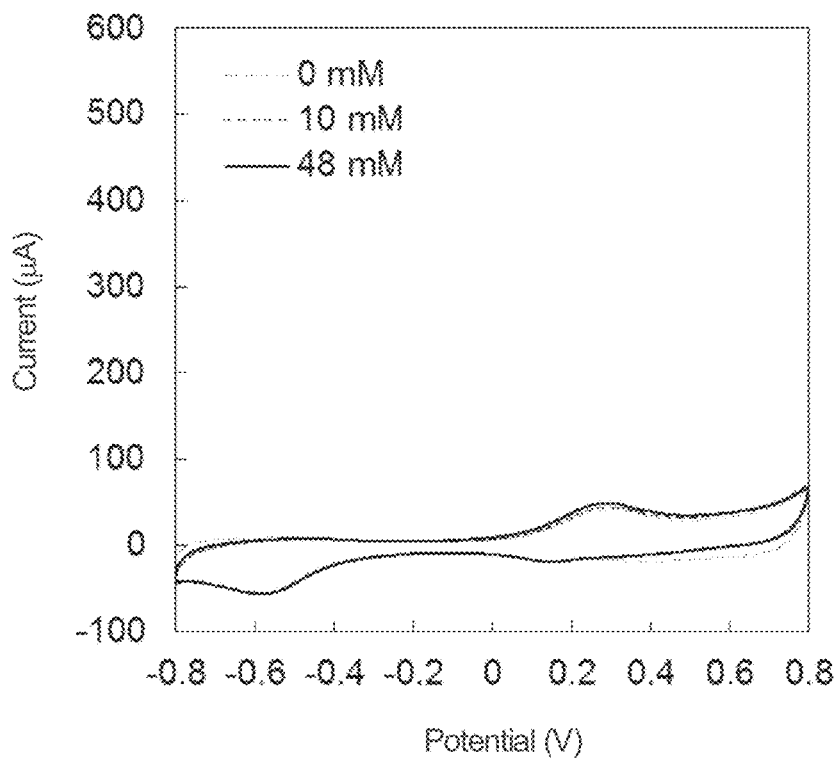
FIG. 10 shows cyclic voltammograms measured without adding thymol to a buffer in Example 4.
Figure 11:
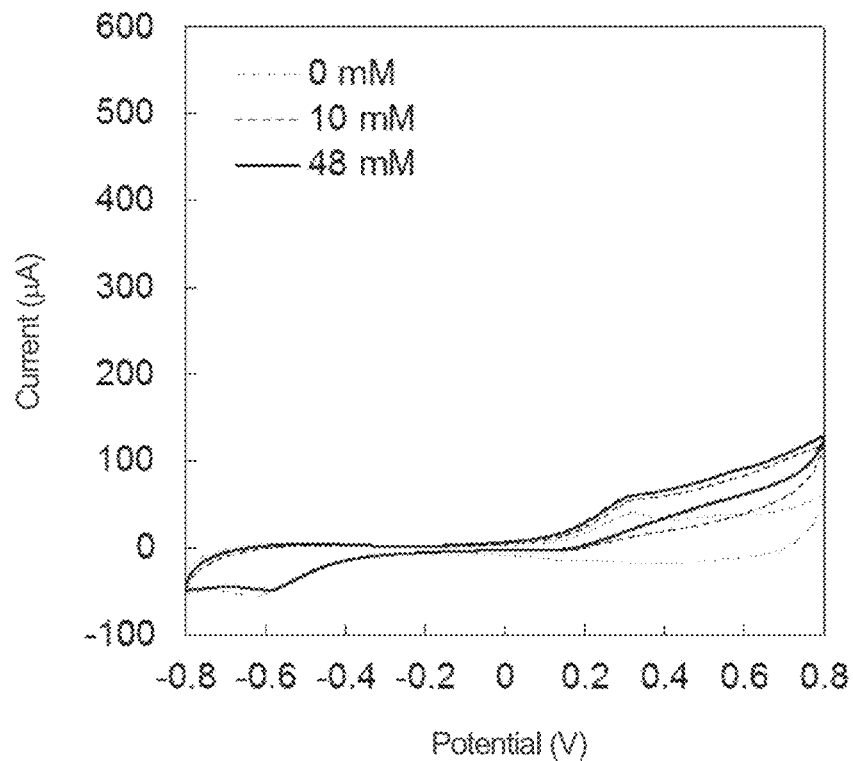
FIG. 11 shows cyclic voltammograms measured while adding thymol to a buffer to 0.00001% (w/v) in Example 4.
Figure 12:
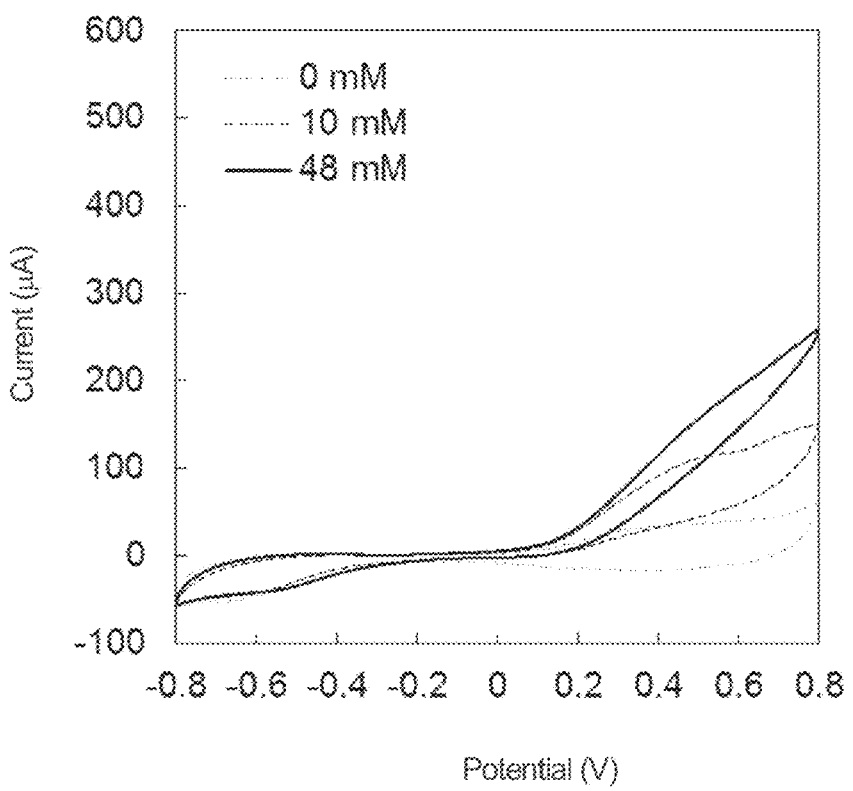
FIG. 12 shows cyclic voltammograms measured while adding thymol to a buffer to 0.0001% (w/v) in Example 4.
Figure 13:
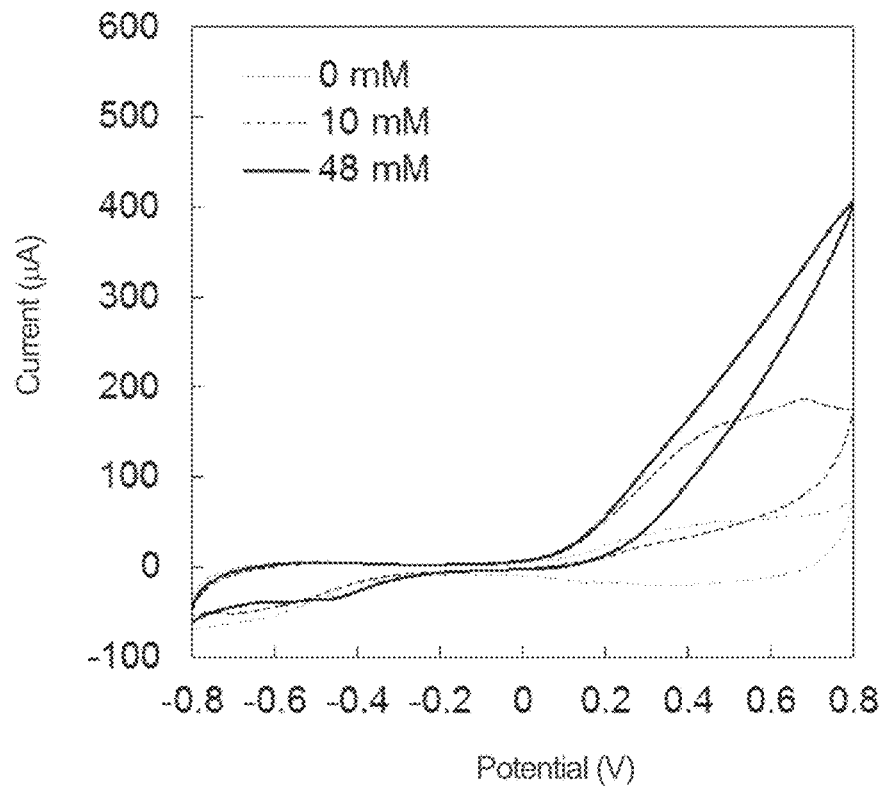
FIG. 13 shows cyclic voltammograms measured while adding thymol to a buffer to 0.001% (w/v) in Example 4.
Figure 14:
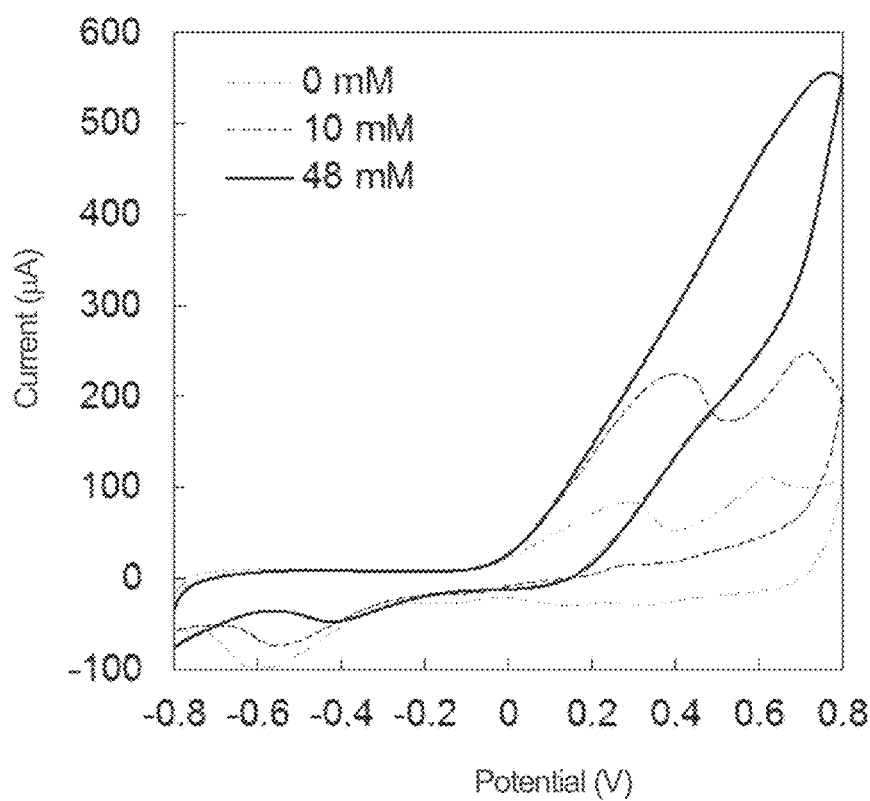
FIG. 14 shows cyclic voltammograms measured while adding thymol to a buffer to 0.01% (w/v) in Example 4.

Cyclic voltammetry measurement was performed in the same manner as in Example 3, except that thymol was not added to a 40 mM sodium phosphate buffer (pH 7.4). FIG. 9 shows the obtained cyclic voltammograms. In the cyclic voltammograms, the current values at +0.6 V when sweeping from −0.8 V to +0.8 V were as shown in Table 6 below.

TABLE 6

| Compound added | Current value (μA) | | |
| --- | --- | --- | --- |
|  | (a) 0 mM glucose | (b) 48 mM glucose | (b)-(a) |
| Not added | 14 | 31 | 17 |

As shown in Example 3 and Comparative Example 3, it was confirmed that the current could also be measured by adding thymol to the buffer, instead of immobilizing thymol on the electrode. These results support that the compounds having an aromatic ring skeleton mediate and promote electron transfer between the coenzyme FAD and the carbon nanotubes.

Example 4

An electrode tip having a 9 mm$^2$ working electrode section was produced using a sheet obtained by depositing gold on a PET substrate, in the same manner as in Example 1. To the working electrode section, 5 μL of a water dispersion containing 2% (w/v) sodium cholate and 0.15% (w/v) single-walled carbon nanotubes (outer diameter: 1.1 to 1.7 nm) was added dropwise and dried. After drying the carbon nanotube dispersion, 5 μL of FADGDH (having the amino acid sequence of SEQ ID No. 2; 20 U/μL) dissolved in ultrapure water was added dropwise to the working electrode section and dried.

After drying the FADGDH liquid, 5 μL of 3% (w/v) Nafion liquid was added dropwise to the working electrode section and dried to immobilize the carbon nanotubes and FADGDH on the working electrode.

Then, a 10% (w/v) thymol solution dissolved in 100% ethanol was added to a 40 mM sodium phosphate buffer (pH 7.4), and thymol-containing buffers with four concentrations (0.00001, 0.0001, 0.001, and 0.01 (w/v)) were prepared.

The electrode tip produced above was set as the working electrode of an electrochemical analyzer (ALS/CHI 660B), a silver/silver chloride electrode was set as the reference electrode, and a platinum wire was set as the counter electrode. These electrodes were immersed in the thymol-containing buffer at any of the above concentrations, or in a 40 mM sodium phosphate buffer (pH 7.4), and cyclic voltammetry measurement was performed. FIGS. 10 to 14 show the cyclic voltammograms measured at glucose concentrations of 0 mM, 10 mM, and 48 mM. The thymol concentration (w/v) is 0% in FIG. 10, 0.00001% in FIG. 11, 0.0001% in FIG. 12, 0.001% in FIGS. 13, and 0.01% in FIG. 14. In the cyclic voltammograms, the current values at +0.6 V when sweeping from −0.8 V to +0.8 V were as shown in Table 7 below.

TABLE 7

| Thymol concentration (% (w/v)) | Current value (μA) | | |
| --- | --- | --- | --- |
|  | (a) 0 mM glucose | (b) 48 mM glucose | (b)-(a) |
| 0 (not added) | 37 | 42 | 5 |
| 0.00001 | 37 | 86 | 49 |

TABLE 7-continued

| Thymol concentration (% (w/v)) | Current value (μA) | | |
| --- | --- | --- | --- |
|  | (a) 0 mM glucose | (b) 48 mM glucose | (b)-(a) |
| 0.0001 | 41 | 202 | 161 |
| 0.001 | 55 | 287 | 232 |
| 0.01 | 115 | 477 | 362 |

As described above, it was revealed that the current could also be measured by adding a very small amount (0.00001% (w/v)) of thymol to the buffer even under the conditions in which the current could not be measured only by immobilizing the enzyme and the carbon nanotubes on the working electrode section. It was also revealed that 60% or more of the maximum current value obtained by adding thymol was measured by adding thymol to the buffer to 0.001% (w/v).

Example 5

Any of the following compounds (11) to (14) was added and dissolved in a 40 mM sodium phosphate buffer (pH 7.4) to 0.1% (w/v).

(11) aniline
(12) o-cresol
(13) m-cresol
(14) p-cresol

An electrode tip produced in the same manner as in Example 1 was set as the working electrode of an electrochemical analyzer (ALS/CHI 660B), a silver/silver chloride electrode was set as the reference electrode, and a platinum wire was set as the counter electrode. These electrodes were immersed in the sodium phosphate buffer in which any one of (11) to (14) was dissolved, or in a 40 mM sodium phosphate buffer (pH 7.4). Cyclic voltammetry measurement was performed when glucose was not added to this buffer (0 mM), or when glucose was added at 48 mM. In the obtained cyclic voltammograms, the current values at +0.6 V when sweeping from −0.8 V to +0.8 V were as shown in Table 8 below.

TABLE 8

| Compound added | Current value (μA) | | |
| --- | --- | --- | --- |
|  | (a) 0 mM glucose | (b) 48 mM glucose | (b)-(a) |
| (11) Aniline | 203 | 520 | 317 |
| (12) o-cresol | 269 | 530 | 261 |
| (13) m-cresol | 205 | 419 | 214 |
| (14) p-cresol | 248 | 316 | 68 |
| Not added | 26 | 31 | 5 |

As described above, it was revealed that the current could be measured by adding compounds (11) to (14) even under the conditions in which the current could not be measured only by immobilizing the enzyme and the carbon nanotubes on the working electrode section.

Example 6

An electrode tip having a 9 mm$^2$ working electrode section was produced using a sheet obtained by depositing gold on a PET substrate, in the same manner as in Example 1. To the working electrode section, 5 μL of a water dispersion containing 2% (w/v) sodium cholate and 0.15% (w/v) single-walled carbon nanotubes (outer diameter: 1.1 to 1.7 nm) was added dropwise and dried. After drying the carbon nanotube dispersion, 5 µL of FADGDH (having the amino acid sequence of SEQ ID No. 2; 20 U/µL) dissolved in ultrapure water was added dropwise to the working electrode section and dried. After drying the FADGDH liquid, 5 µL of each of the following compounds (15) to (33) (each 1% (w/v) liquid) was added dropwise to the working electrode section and dried.

(15) leucoquinizarin (dissolved in 80% (v/v) acetone)
(16) carvacrol (dissolved in 50% (v/v) ethanol)
(17) 1,5-naphthalene diol (dissolved in 50% (v/v) ethanol)
(18) 4-isopropyl-3-methylphenol (dissolved in 50% (v/v) ethanol)
(19) 2-isopropylphenol (dissolved in 50% (v/v) ethanol)
(20) 4-isopropylphenol (dissolved in 50% (v/v) ethanol)
(21) 1-naphthol (dissolved in 50% (v/v) ethanol)
(22) 2-tert-butyl-5-methylphenol (dissolved in 50% (v/v) ethanol)
(23) 2,4,6-trimethylphenol (dissolved in 50% (v/v) ethanol)
(24) 2,6-diisopropylphenol (dissolved in 50% (v/v) ethanol)
(25) 2-tert-butyl-4-ethylphenol (dissolved in 50% (v/v) ethanol)
(26) 6-tert-butyl-2,4-xylenol (dissolved in 50% (v/v) ethanol)
(27) 2-tert-butyl-4-methylphenol (dissolved in 50% (v/v) ethanol)
(28) 2-tert-butyl-6-methylphenol (dissolved in 50% (v/v) ethanol)
(29) 2,4-di-tert-butylphenol (dissolved in 50% (v/v) ethanol)
(30) 2,4-di-tert-butyl-5-methylphenol (dissolved in 50% (v/v) ethanol)
(31) bis(p-hydroxyphenyl)methane (dissolved in 50% (v/v) ethanol)
(32) 3-tert-butylphenol (dissolved in 50% (v/v) ethanol)
(33) 2-isopropyl-5-methylanisole (dissolved in 80% (v/v) ethanol)

After drying the liquids of compounds (15) to (33), 5 µL of 3% (w/v) Nafion liquid was added dropwise to the working electrode section and dried to immobilize the carbon nanotubes and FADGDH on the working electrode.

The electrode tip produced above was set as the working electrode of an electrochemical analyzer (ALS/CHI 660B), a silver/silver chloride electrode was set as the reference electrode, and a platinum wire was set as the counter electrode. These three electrodes were immersed in a 40 mM sodium phosphate buffer (pH 7.4). Cyclic voltammetry measurement was performed when glucose was not added to this buffer (0 mM), or when glucose was added at 48 mM. In the obtained cyclic voltammograms, the current values at +0.6 V when sweeping from −0.8 V to +0.8 V were as shown in Table 9 below.

TABLE 9

| | Current value (µA) | | |
|---|---|---|---|
| Compound added | (a) 0 mM glucose | (b) 48 mM glucose | (b)-(a) |
| (15) Leucoquinizarin | 59 | 397 | 338 |
| (16) Carvacrol | 90 | 591 | 501 |
| (17) 1,5-Naphthalene diol | 323 | 436 | 113 |
| (18) 4-Isopropyl-3-methylphenol | 72 | 497 | 425 |
| (19) 2-Isopropylphenol | 65 | 473 | 408 |

TABLE 9-continued

| | Current value (µA) | | |
|---|---|---|---|
| Compound added | (a) 0 mM glucose | (b) 48 mM glucose | (b)-(a) |
| (20) 4-Isopropylphenol | 63 | 335 | 272 |
| (21) 1-Naphthol | 81 | 539 | 458 |
| (22) 2-Tert-butyl-5-methylphenol | 70 | 325 | 255 |
| (23) 2,4,6-Trimethylphenol | 71 | 384 | 313 |
| (24) 2,6-Diisopropylphenol | 48 | 199 | 151 |
| (25) 2-Tert-butyl-4-ethylphenol | 59 | 310 | 251 |
| (26) 6-Tert-butyl-2,4-xylenol | 78 | 239 | 161 |
| (27) 2-Tert-butyl-4-methylphenol | 54 | 315 | 261 |
| (28) 2-Tert-butyl-6-methylphenol | 48 | 226 | 178 |
| (29) 2,4-Di-tert-butylphenol | 61 | 257 | 196 |
| (30) 2,4-Di-tert-butyl-5-methylphenol | 50 | 215 | 165 |
| (31) Bis(p-hydroxyphenyl)methane | 187 | 83 | 104 |
| (32) 3-Tert-butylphenol | 382 | 52 | 330 |
| (33) 2-Isopropyl-5-methylanisole | 72 | 43 | 29 |

Comparative Example 4

Cyclic voltammograms were measured in the same manner as in Example 3, except that compounds (15) to (33) were replaced with the following compound (34).

(34) piperylene (dissolved in 100% acetone)

In the obtained cyclic voltammograms, the current values at +0.6 V when sweeping from −0.8 V to +0.8 V were as shown in Table 10 below.

TABLE 10

| | Current value (µA) | | |
|---|---|---|---|
| Compound added | (a) 0 mM glucose | (b) 48 mM glucose | (b)-(a) |
| (34) Piperylene | 21 | 28 | 7 |
| Not added | 22 | 30 | 8 |

The results of Example 6 and Comparative Example 4 revealed that the current could be measured by adding compounds (15) to (33) even under the conditions in which the current could not be measured only by immobilizing the enzyme and the carbon nanotubes on the working electrode section. On the other hand, it was revealed that the current was not measured when compound (34) was added.

Compounds (15) to (33) all have an aromatic ring skeleton, whereas compound (34) has π electrons but no aromatic ring skeleton. Therefore, it is presumed that due to the aromatic ring skeleton, compounds (15) to (33) mediate and promote electron transfer between the coenzyme FAD and the carbon nanotubes.

Example 7

An electrode tip having a 9 mm² working electrode section was produced using a sheet obtained by depositing gold on a PET substrate, in the same manner as in Example 1. To the working electrode section, 8.2 µL of a water dispersion containing 2% (w/v) sodium cholate and 0.092% (w/v) multi-walled carbon nanotubes (NC7000, Nanocyl, outer diameter: 5 to 15 nm) was added dropwise and dried. After drying the carbon nanotube dispersion, 5 µL of FADGDH (having the amino acid sequence represented by SEQ ID No. 2; 20 U/µL) dissolved in ultrapure water was added dropwise to the working electrode section and dried. After drying the FADGDH liquid, 5 µL of 3% (w/v) Nafion liquid was added dropwise to the working electrode section and dried to immobilize the carbon nanotubes and FAD-GDH on the working electrode. A 10% (w/v) thymol solution dissolved in 100% ethanol was added and mixed with a 40 mM sodium phosphate buffer (pH 7.4) to 0.01% (w/v).

Figure 15:
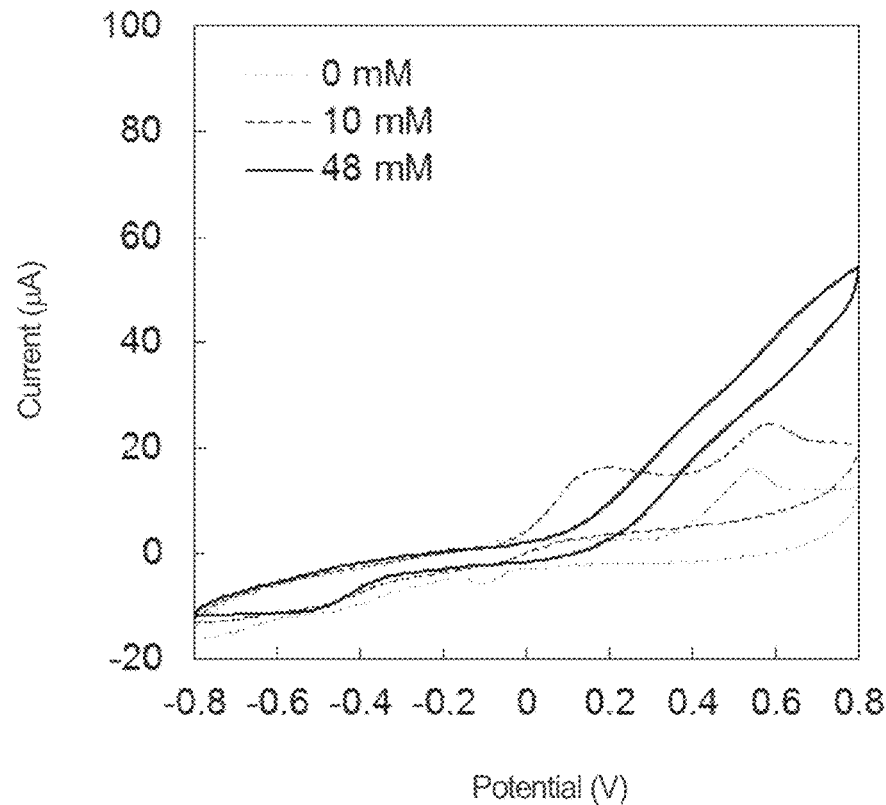
FIG. 15 shows cyclic voltammograms measured while adding thymol to a buffer in Example 7.

The electrode tip produced above was set as the working electrode of an electrochemical analyzer (ALS/CHI 660B), a silver/silver chloride electrode was set as the reference electrode, and a platinum wire was set as the counter electrode. These electrodes were immersed in a sodium phosphate buffer containing 0.01% (w/v) thymol, and cyclic voltammetry measurement was performed. FIG. 15 shows the cyclic voltammograms measured at glucose concentrations of 0 mM, 10 mM, and 48 mM. In the cyclic voltammograms, the current values at +0.6 V when sweeping from −0.8 V to +0.8 V were as shown in Table 11 below.

TABLE 11

| | Current value (μA) | | |
|---|---|---|---|
| Compound added | (a) 0 mM glucose | (b) 48 mM glucose | (b)-(a) |
| Thymol | 14 | 42 | 28 |

Comparative Example 5

Figure 16:
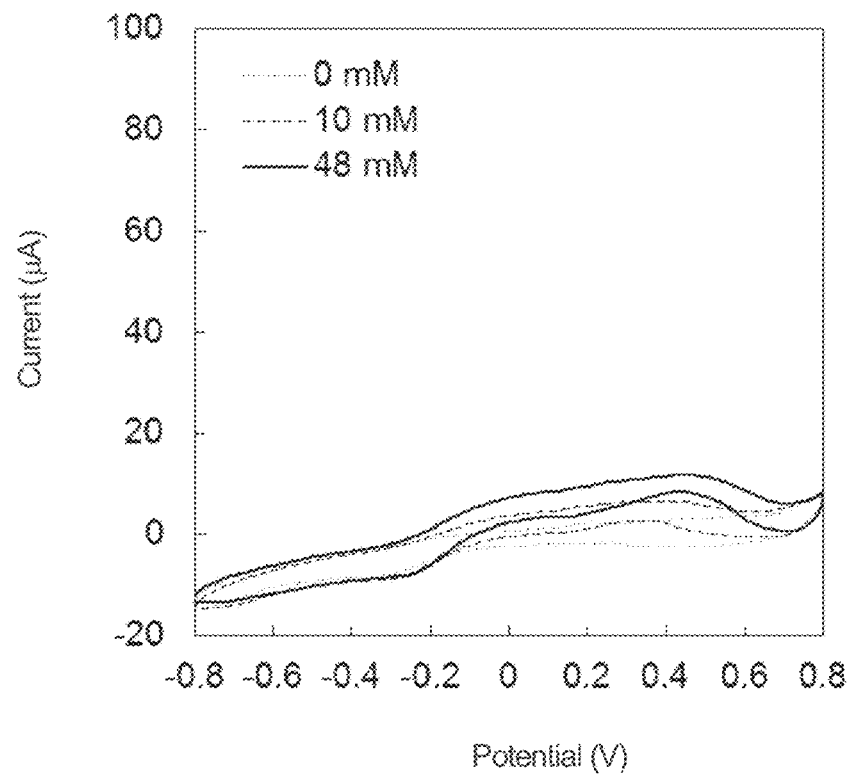
FIG. 16 shows cyclic voltammograms measured without adding thymol to a buffer in Comparative Example 5.

Cyclic voltammetry measurement was performed in the same manner as in Example 4, except that thymol was not added to a 40 mM sodium phosphate buffer (pH 7.4). FIG. 16 shows the obtained cyclic voltammograms. In the cyclic voltammograms, the current values at +0.6 V when sweeping from −0.8 V to +0.8 V were as shown in Table 12 below.

TABLE 12

| | Current value (μA) | | |
|---|---|---|---|
| Compound added | (a) 0 mM glucose | (b) 48 mM glucose | (b)-(a) |
| Not added | 5 | 11 | 6 |

As shown in Example 7 and Comparative Example 5, it was confirmed that the current could be measured by adding thymol to the buffer even when multi-walled carbon nanotubes were used.

Example 8

An electrode tip having a 9 mm² working electrode section was produced using a sheet obtained by depositing gold on a PET substrate, in the same manner as in Example 1. To the working electrode section, 5 μL of a water dispersion containing 2% (w/v) sodium cholate and 0.15% (w/v) single-walled carbon nanotubes (outer diameter: 1.1 to 1.7 nm), or 8.2 μL of a water dispersion containing 2% (w/v) sodium cholate and 0.092% (w/v) multi-walled carbon nanotubes (outer diameter: 5 to 15 nm), was added dropwise and dried. After drying the carbon nanotube dispersion, 5 μL of glucose oxidase (20 U/μL) dissolved in ultrapure water was added dropwise to the working electrode section and dried. After drying the glucose oxidase liquid, 5 μL of 3% (w/v) Nafion liquid was added dropwise to the working electrode section and dried to immobilize the carbon nanotubes and glucose oxidase on the working electrode. A 10% (w/v) thymol solution dissolved in 100% ethanol was added and mixed with a 40 mM sodium phosphate buffer (pH 7.4) to 0.01% (w/v).

Figure 17:
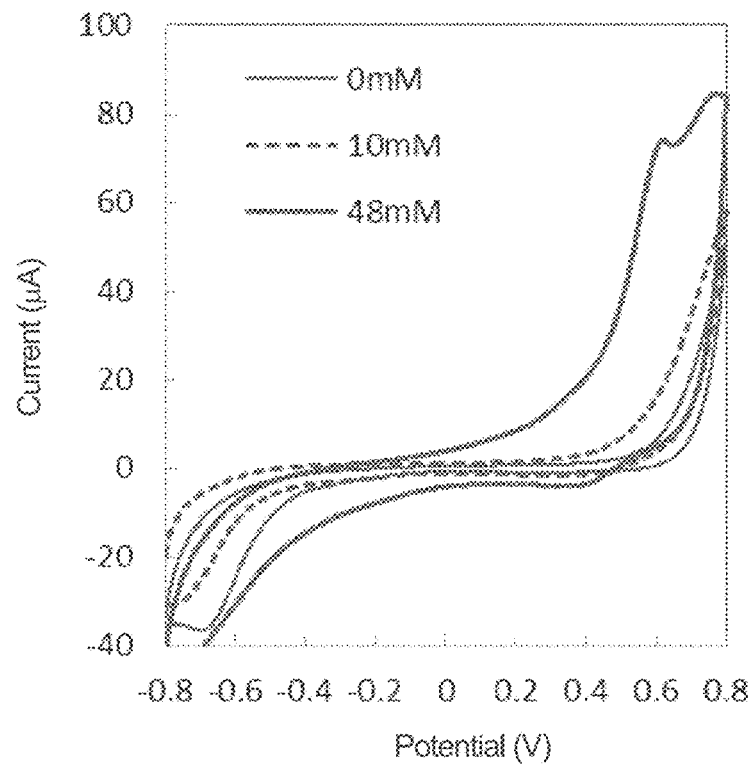
FIG. 17 shows cyclic voltammograms measured while loading single-walled carbon nanotubes on the working electrode section in Example 8.
Figure 18:
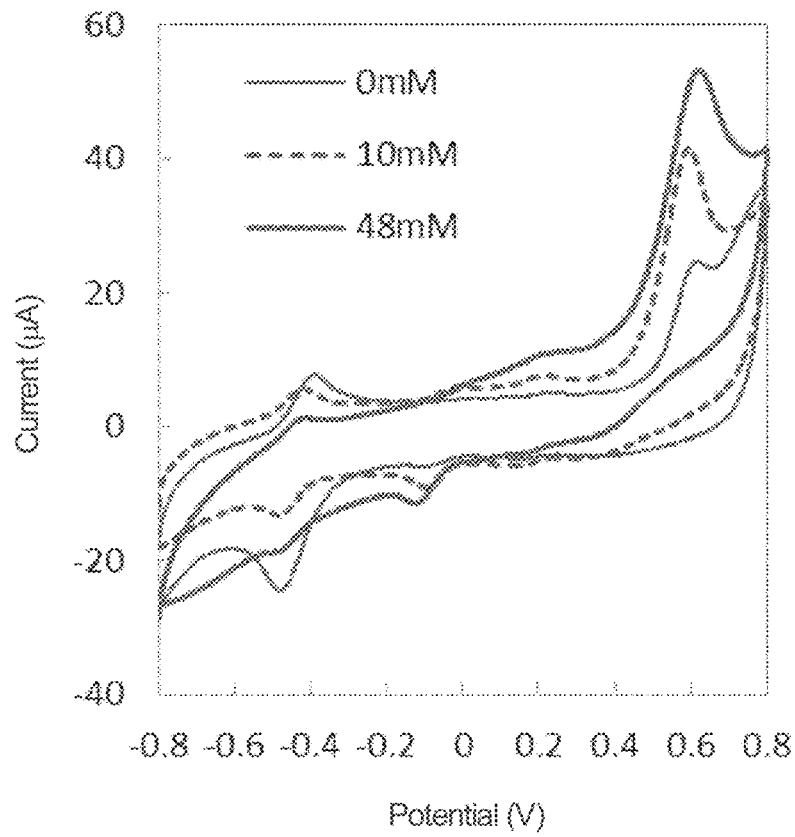
FIG. 18 shows cyclic voltammograms measured while loading multi-walled carbon nanotubes on the working electrode section in Example 8.

The electrode tip produced above was set as the working electrode of an electrochemical analyzer (ALS/CHI 660B), a silver/silver chloride electrode was set as the reference electrode, and a platinum wire was set as the counter electrode. These electrodes were immersed in a sodium phosphate buffer containing 0.01% (w/v) thymol, and cyclic voltammetry measurement was performed. The cyclic voltammograms measured at glucose concentrations of 0 mM, 10 mM, and 48 mM are shown in FIG. 17 (single-walled carbon nanotubes) and FIG. 18 (multi-walled carbon nanotubes). In the cyclic voltammograms, the current values at +0.6 V when sweeping from −0.8 V to +0.8 V were as shown in Table 13 below.

TABLE 13

| | Current value (μA) | | |
|---|---|---|---|
| Carbon nanotubes | (a) 0 mM glucose | (b) 48 mM glucose | (b)-(a) |
| Single-walled carbon nanotubes | 6 | 72 | 66 |
| Multi-walled carbon nanotubes | 24 | 52 | 28 |

Comparative Example 6

Figure 19:
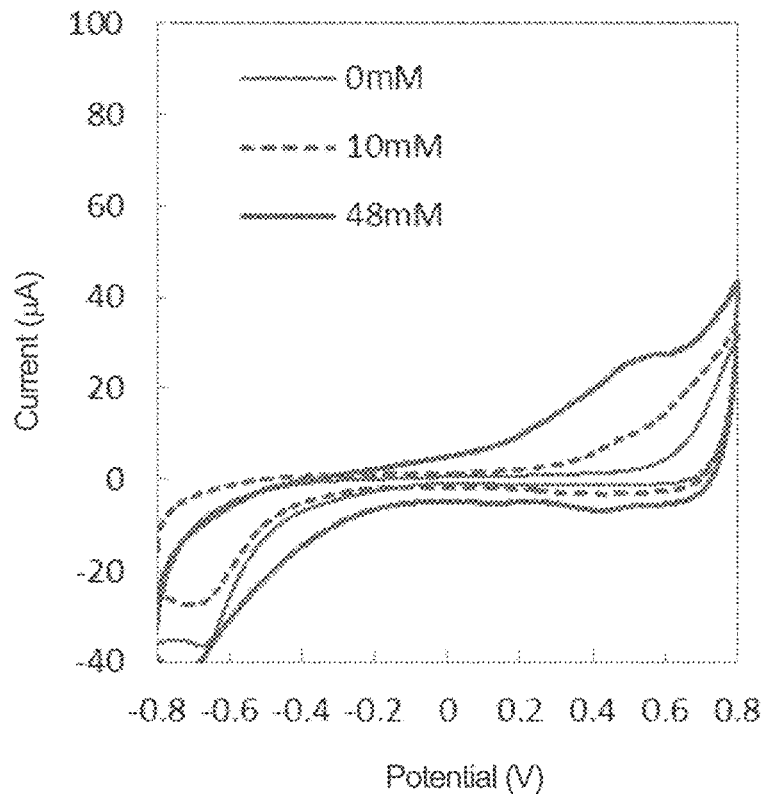
FIG. 19 shows cyclic voltammograms measured while loading single-walled carbon nanotubes on the working electrode section in Comparative Example 6.
Figure 20:
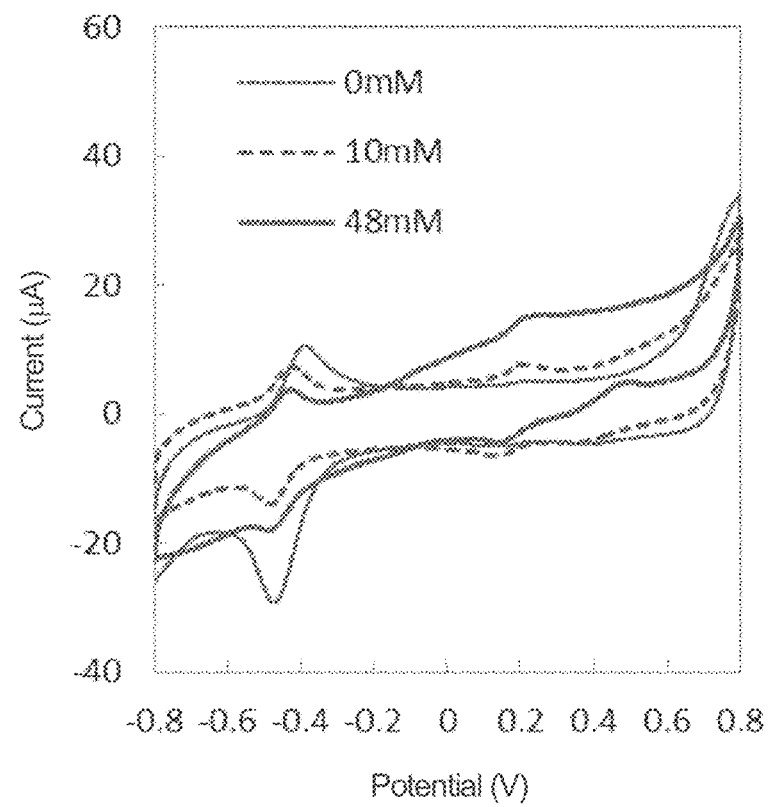
FIG. 20 shows cyclic voltammograms measured while loading multi-walled carbon nanotubes on the working electrode section in Comparative Example 6.

Cyclic voltammetry measurement was performed in the same manner as in Example 8, except that thymol was not added to a 40 mM sodium phosphate buffer (pH 7.4). The obtained cyclic voltammograms are shown in FIG. 19 (single-walled carbon nanotubes) and FIG. 20 (multi-walled carbon nanotubes). In the cyclic voltammograms, the current values at +0.6 V when sweeping from −0.8 V to +0.8 V were as shown in Table 14 below.

TABLE 14

| | Current value (μA) | | |
|---|---|---|---|
| Carbon nanotubes | (a) 0 mM glucose | (b) 48 mM glucose | (b)-(a) |
| Single-walled carbon nanotubes | 4 | 27 | 23 |
| Multi-walled carbon nanotubes | 10 | 19 | 9 |

As shown in Example 8 and Comparative Example 6, it was confirmed that the addition of thymol to the buffer increased the current values, even when using either single-walled carbon nanotubes or multi-walled carbon nanotubes.

Example 9

An electrode tip having a 9 mm² working electrode section was produced using a sheet obtained by depositing gold on a PET substrate, in the same manner as in Example 1. To the working electrode section, 5 μL of a water dispersion containing 2% (w/v) sodium cholate and 0.15% (w/v) single-walled carbon nanotubes (outer diameter: 1.1 to 1.7 nm), or 8.2 μL of a water dispersion containing 2% (w/v) sodium cholate and 0.092% (w/v) multi-walled carbon nanotubes (outer diameter: 5 to 15 nm), was added dropwise and dried. After drying the carbon nanotube dispersion, 5 μL of lactate oxidase (having the amino acid sequence of SEQ ID No. 7; 20 U/μL) dissolved in ultrapure water was added dropwise to the working electrode section and dried. After drying the lactate oxidase liquid, 5 μL of 3% (w/v) Nafion liquid was added dropwise to the working electrode section and dried to immobilize the carbon nanotubes and lactate oxidase on the working electrode. A 10% (w/v) thymol solution dissolved in 100% ethanol was added and mixed with a 40 mM sodium phosphate buffer (pH 7.4) to 0.01% (w/v).

Figure 21:
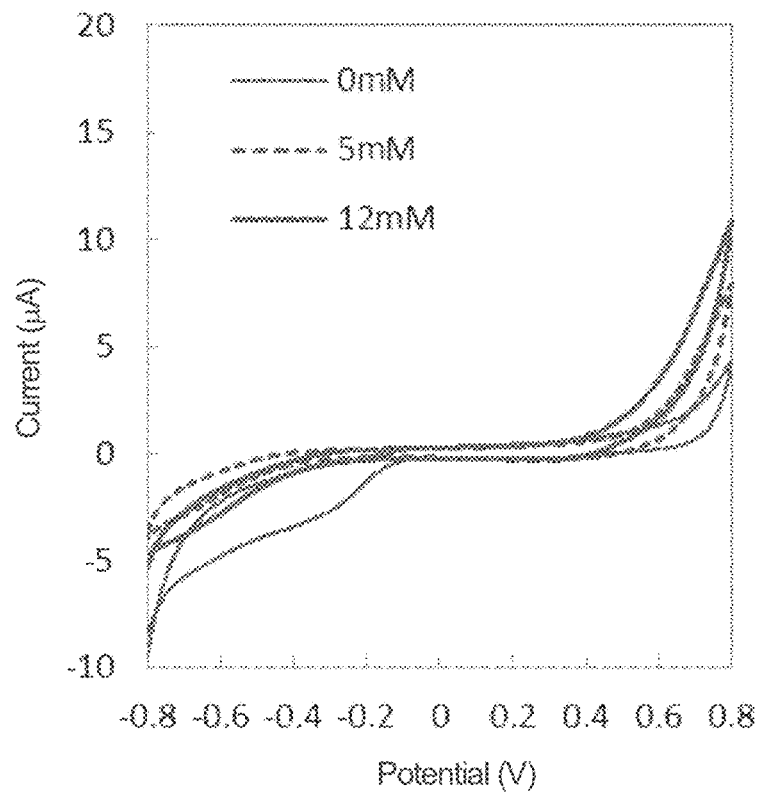
FIG. 21 shows cyclic voltammograms measured while loading single-walled carbon nanotubes on the working electrode section in Example 9.
Figure 22:
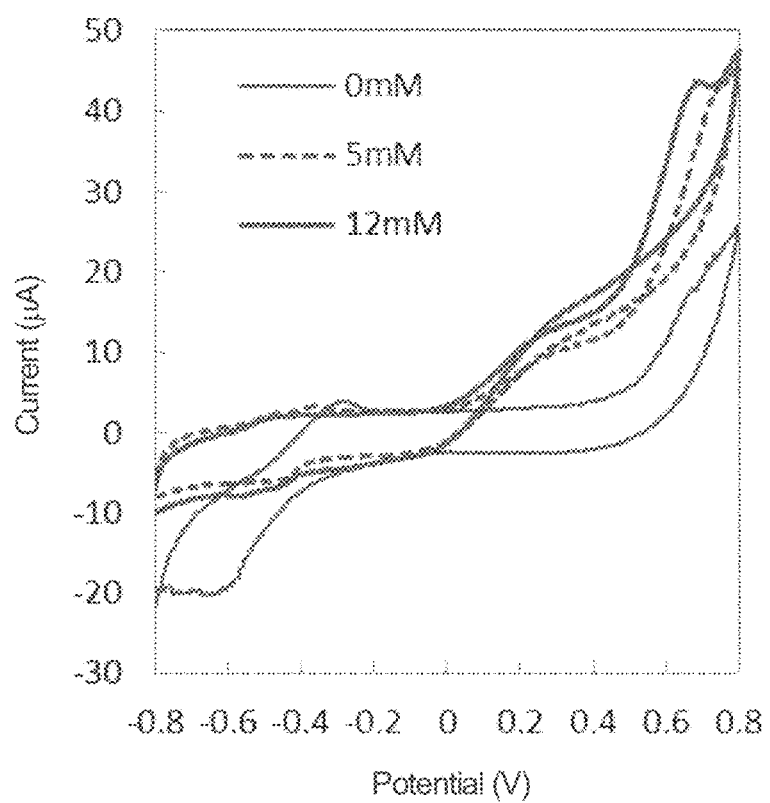
FIG. 22 shows cyclic voltammograms measured while loading multi-walled carbon nanotubes on the working electrode section in Example 9.

The electrode tip produced above was set as the working electrode of an electrochemical analyzer (ALS/CHI 660B), a silver/silver chloride electrode was set as the reference electrode, and a platinum wire was set as the counter electrode. These electrodes were immersed in a sodium phosphate buffer containing 0.01% (w/v) thymol, and cyclic voltammetry measurement was performed. The cyclic voltammograms measured at lactic acid concentrations of 0 mM, 5 mM, and 12 mM are shown in FIG. 21 (single-walled carbon nanotubes) and FIG. 22 (multi-walled carbon nanotubes). In the cyclic voltammograms, the current values at +0.6 V when sweeping from −0.8 V to +0.8 V were as shown in Table 15 below.

TABLE 15

| Carbon nanotubes | Current value (μA) | | |
|---|---|---|---|
| | (a) 0 mM lactic acid | (b) 12 mM lactic acid | (b)-(a) |
| Single-walled carbon nanotubes | 1.3 | 3.4 | 2.1 |
| Multi-walled carbon nanotubes | 11.3 | 33.2 | 21.9 |

Comparative Example 7

Figure 23:
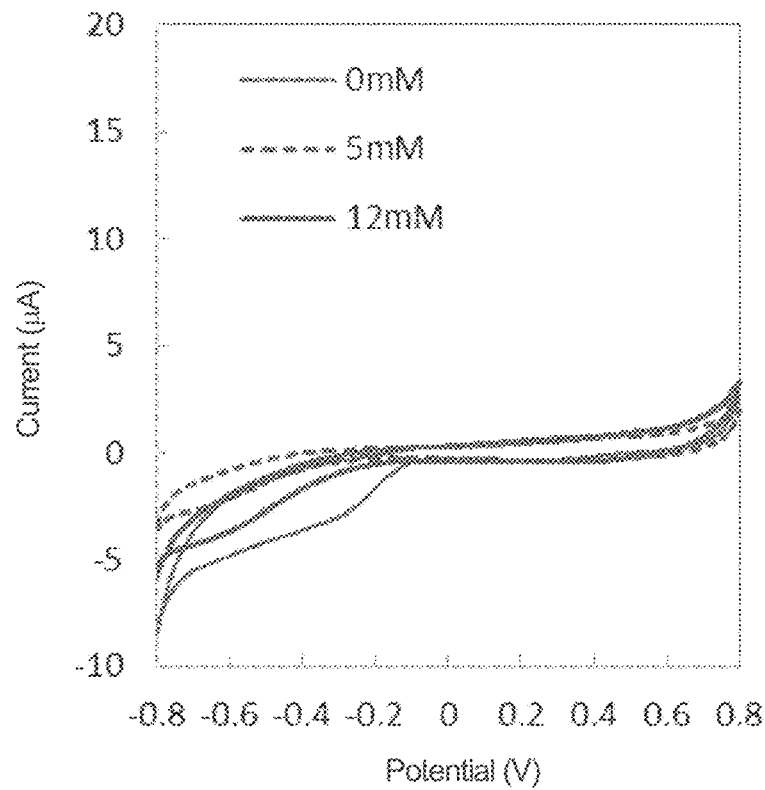
FIG. 23 shows cyclic voltammograms measured while loading single-walled carbon nanotubes on the working electrode section in Comparative Example 7.
Figure 24:
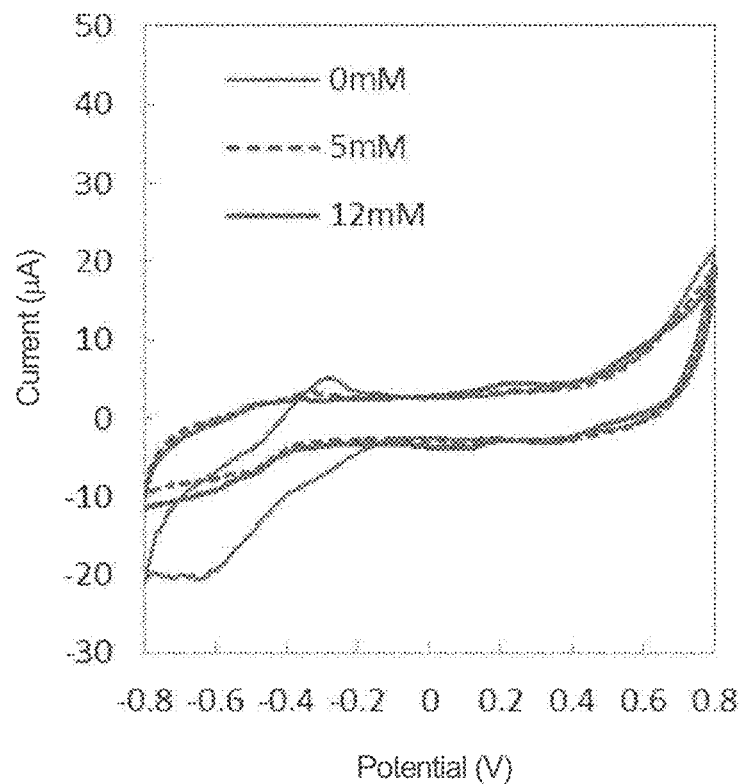
FIG. 24 shows cyclic voltammograms measured while loading multi-walled carbon nanotubes on the working electrode section in Comparative Example 7.

Cyclic voltammetry measurement was performed in the same manner as in Example 8, except that thymol was not added to a 40 mM sodium phosphate buffer (pH 7.4). The obtained cyclic voltammograms are shown in FIG. 23 (single-walled carbon nanotubes) and FIG. 24 (multi-walled carbon nanotubes). In the cyclic voltammograms, the current values at +0.6 V when sweeping from −0.8 V to +0.8 V were as shown in Table 16 below.

TABLE 16

| Carbon nanotubes | Current value (μA) | | |
|---|---|---|---|
| | (a) 0 mM lactic acid | (b) 12 mM lactic acid | (b)-(a) |
| Single-walled carbon nanotubes | 1.1 | 1.1 | 0.0 |
| Multi-walled carbon nanotubes | 8.4 | 9.2 | 0.8 |

As shown in Example 9 and Comparative Example 7, it was confirmed that the addition of thymol to the buffer increased the current values, even when using either single-walled carbon nanotubes or multi-walled carbon nanotubes.

Sequence Listing

The invention claimed is:

1. An electrode loaded with nanocarbon, a compound having an aromatic ring skeleton, and an enzyme on a substrate, wherein the compound having an aromatic ring skeleton is selected from the group consisting of thymol, phenol, bis(4-hydroxyphenyl)sulfone, tyrosine disodium hydrate, sodium salicylate, 5-hydroxyindole, aniline (CAS Registry No. 62-53-3), leucoquinizarin, carvacrol, 1,5-naphthalene diol, 4-isopropyl-3-methylphenol, 2-isopropylphenol, 4-isopropylphenol, 1-naphthol, 2-tert-butyl-5-methylphenol, 2,4,6-trimethylphenol, 2,6-diisopropylphenol, 2-tert-butyl-4-ethylphenol, 6-tert-butyl-2,4-xylenol, 2-tert-butyl-4-methylphenol, 2-tert-butyl-6-methylphenol, 2,4-di-tert-butylphenol, 2,4-di-tert-butyl-5-methylphenol, bis(p-hydroxyphenyl)methane, 3-tert-butylphenol, 2-isopropyl-5-methylanisole, o-cresol, m-cresol, and p-cresol.

2. The electrode according to claim 1, wherein the nanocarbon is a carbon nanotube.

3. The electrode according to claim 1, wherein the carbon nanotube is a single-walled carbon nanotube.

4. The electrode according to claim 1, wherein the enzyme is flavin-binding glucose dehydrogenase.

5. The electrode according to claim 1, further comprising a dispersant loaded on the substrate.

6. The electrode according to claim 1, wherein a thin film of carbon or metal is formed on the substrate.

7. A sensor comprising the electrode according to claim 1.

8. The electrode according to claim 1, wherein the compound having an aromatic ring skeleton is a compound that does not function as a mediator by itself.

9. The electrode according to claim 1, wherein the carbon nanotube is a single-walled carbon nanotube and the enzyme is flavin-binding glucose dehydrogenase.

10. A sensor comprising the electrode according to claim 9.

11. A method for preparing an electrode loaded with nanocarbon, a compound having an aromatic ring skeleton, and an enzyme on a substrate, the method comprising attaching or bringing close the compound having an aromatic ring skeleton to nanocarbon on the substrate, wherein the compound having an aromatic ring skeleton is selected from the group consisting of thymol, phenol, bis(4-hydroxyphenyl)sulfone, tyrosine disodium hydrate, sodium salicylate, 5-hydroxyindole, aniline (CAS Registry No. 62-53-3), leucoquinizarin, carvacrol, 1,5-naphthalene diol, 4-isopropyl-3-methylphenol, 2-isopropylphenol, 4-isopropylphenol, 1-naphthol, 2-tert-butyl-5-methylphenol, 2,4,6-trimethylphenol, 2,6-diisopropylphenol, 2-tert-butyl-4-ethylphenol, 6-tert-butyl-2,4-xylenol, 2-tert-butyl-4-methylphenol, 2-tert-butyl-6-methylphenol, 2,4-di-tert-butylphenol, 2,4-di-tert-butyl-5-methylphenol, bis(p-hydroxyphenyl)methane, 3-tert-butylphenol, 2-isopropyl-5-methylanisole, o-cresol, m-cresol, and p-cresol.

12. The method according to claim 11, wherein the compound having an aromatic ring skeleton is a compound that does not function as a mediator by itself.

13. The method according to claim 11, wherein the nanocarbon is a carbon nanotube.

14. The method according to claim 11, wherein the nanocarbon is a single-walled carbon nanotube.

15. The method according to claim 11, wherein the enzyme is flavin-binding glucose dehydrogenase.

16. The method according to claim 11, wherein the substrate is a substrate on which a thin film of carbon or metal is formed.

17. The method according to claim 11, wherein the carbon nanotube is a single-walled carbon nanotube and the enzyme is flavin-binding glucose dehydrogenase.

* * * * *

SEQUENCE LISTING

```
<160> NUMBER OF SEQ ID NOS: 7

<210> SEQ ID NO 1
<211> LENGTH: 593
<212> TYPE: PRT
<213> ORGANISM: Aspergillus oryzae

<400> SEQUENCE: 1

Met Leu Phe Ser Leu Ala Phe Leu Ser Ala Leu Ser Leu Ala Thr Ala
1               5                   10                  15

Ser Pro Ala Gly Arg Ala Lys Asn Thr Thr Tyr Asp Tyr Ile Val
            20                  25                  30

Val Gly Gly Gly Thr Ser Gly Leu Val Val Ala Asn Arg Leu Ser Glu
        35                  40                  45

Asn Pro Asp Val Ser Val Leu Leu Leu Glu Ala Gly Ala Ser Val Phe
    50                  55                  60

Asn Asn Pro Asp Val Thr Asn Ala Asn Gly Tyr Gly Leu Ala Phe Gly
65                  70                  75                  80

Ser Ala Ile Asp Trp Gln Tyr Gln Ser Ile Asn Gln Ser Tyr Ala Gly
                85                  90                  95

Gly Lys Gln Gln Val Leu Arg Ala Gly Lys Ala Leu Gly Gly Thr Ser
            100                 105                 110

Thr Ile Asn Gly Met Ala Tyr Thr Arg Ala Glu Asp Val Gln Ile Asp
        115                 120                 125

Val Trp Gln Lys Leu Gly Asn Glu Gly Trp Thr Trp Lys Asp Leu Leu
    130                 135                 140

Pro Tyr Tyr Leu Lys Ser Glu Asn Leu Thr Ala Pro Thr Ser Ser Gln
145                 150                 155                 160
```

```
Val Ala Ala Gly Ala Ala Tyr Asn Pro Ala Val Asn Gly Lys Glu Gly
                165                 170                 175

Pro Leu Lys Val Gly Trp Ser Gly Ser Leu Ala Ser Gly Asn Leu Ser
            180                 185                 190

Val Ala Leu Asn Arg Thr Phe Gln Ala Ala Gly Val Pro Trp Val Glu
        195                 200                 205

Asp Val Asn Gly Gly Lys Met Arg Gly Phe Asn Ile Tyr Pro Ser Thr
    210                 215                 220

Leu Asp Val Asp Leu Asn Val Arg Glu Asp Ala Ala Arg Ala Tyr Tyr
225                 230                 235                 240

Phe Pro Tyr Asp Asp Arg Lys Asn Leu His Leu Leu Glu Asn Thr Thr
                245                 250                 255

Ala Asn Arg Leu Phe Trp Lys Asn Gly Ser Ala Glu Glu Ala Ile Ala
            260                 265                 270

Asp Gly Val Glu Ile Thr Ser Ala Asp Gly Lys Val Thr Arg Val His
        275                 280                 285

Ala Lys Lys Glu Val Ile Ile Ser Ala Gly Ala Leu Arg Ser Pro Leu
    290                 295                 300

Ile Leu Glu Leu Ser Gly Val Gly Asn Pro Thr Ile Leu Lys Lys Asn
305                 310                 315                 320

Asn Ile Thr Pro Arg Val Asp Leu Pro Thr Val Gly Glu Asn Leu Gln
                325                 330                 335

Asp Gln Phe Asn Asn Gly Met Ala Gly Glu Gly Tyr Gly Val Leu Ala
            340                 345                 350

Gly Ala Ser Thr Val Thr Tyr Pro Ser Ile Ser Asp Val Phe Gly Asn
        355                 360                 365

Glu Thr Asp Ser Ile Val Ala Ser Leu Arg Ser Gln Leu Ser Asp Tyr
    370                 375                 380

Ala Ala Ala Thr Val Lys Val Ser Asn Gly His Met Lys Gln Glu Asp
385                 390                 395                 400

Leu Glu Arg Leu Tyr Gln Leu Gln Phe Asp Leu Ile Val Lys Asp Lys
                405                 410                 415

Val Pro Ile Ala Glu Ile Leu Phe His Pro Gly Gly Gly Asn Ala Val
            420                 425                 430

Ser Ser Glu Phe Trp Gly Leu Leu Pro Phe Ala Arg Gly Asn Ile His
        435                 440                 445

Ile Ser Ser Asn Asp Pro Thr Ala Pro Ala Ile Asn Pro Asn Tyr
    450                 455                 460

Phe Met Phe Glu Trp Asp Gly Lys Ser Gln Ala Gly Ile Ala Lys Tyr
465                 470                 475                 480

Ile Arg Lys Ile Leu Arg Ser Ala Pro Leu Asn Lys Leu Ile Ala Lys
                485                 490                 495

Glu Thr Lys Pro Gly Leu Ser Glu Ile Pro Ala Thr Ala Ala Asp Glu
            500                 505                 510

Lys Trp Val Glu Trp Leu Lys Ala Asn Tyr Arg Ser Asn Phe His Pro
        515                 520                 525

Val Gly Thr Ala Ala Met Met Pro Arg Ser Ile Gly Gly Val Val Asp
    530                 535                 540

Asn Arg Leu Arg Val Tyr Gly Thr Ser Asn Val Arg Val Val Asp Ala
545                 550                 555                 560

Ser Val Leu Pro Phe Gln Val Cys Gly His Leu Val Ser Thr Leu Tyr
                565                 570                 575
```

```
Ala Val Ala Glu Arg Ala Ser Asp Leu Ile Lys Glu Asp Ala Lys Ser
            580                 585                 590

Ala
```

<210> SEQ ID NO 2
<211> LENGTH: 635
<212> TYPE: PRT
<213> ORGANISM: Mucor hiemalis

<400> SEQUENCE: 2

```
Met Lys Ile Ser Val Ala Ile Val Thr Ile Ala Ala Ala Phe Ala Ser
1               5                   10                  15

Phe Ala Asn Ala Gln Lys Thr Ala Thr Ser Asn Thr Tyr Asp Tyr Val
            20                  25                  30

Ile Val Gly Gly Gly Val Gly Gly Leu Ala Leu Ala Ser Arg Leu Ser
        35                  40                  45

Glu Asp Lys Ser Val Thr Val Ala Val Leu Glu Ala Gly Pro Asn Ala
    50                  55                  60

Asp Glu Gln Phe Val Val Tyr Ala Pro Gly Met Tyr Gly Gln Ala Val
65                  70                  75                  80

Gly Thr Asp Leu Cys Pro Leu Arg Pro Thr Val Pro Gln Glu Ala Met
                85                  90                  95

Asn Asn Arg Thr Leu Thr Ile Ala Thr Gly Lys Leu Leu Gly Gly Gly
            100                 105                 110

Ser Ala Ile Asn Gly Leu Val Trp Thr Arg Gly Ala Leu Lys Asp Phe
        115                 120                 125

Asp Ala Trp Glu Glu Leu Gly Asn Pro Gly Trp Asn Gly Arg Thr Met
    130                 135                 140

Phe Lys Tyr Phe Lys Lys Val Glu Arg Phe His Pro Pro Thr Lys Ala
145                 150                 155                 160

Gln Val Gln Tyr Gly Ala Thr Tyr Gln Lys Gly Val His Gly Lys Asn
                165                 170                 175

Gly Arg Ile Asp Ile Ser Phe Pro Glu Phe Gln Phe Pro Gln Ser Ala
            180                 185                 190

Asn Trp Asn Ala Ser Leu Ala Thr Leu Asp Phe Thr His Gln Gln Asp
        195                 200                 205

Leu Leu Asn Gly Ser Leu His Gly Tyr Ser Thr Thr Pro Asn Thr Leu
    210                 215                 220

Asp Pro Lys Thr Ala Arg Arg Val Asp Ser Tyr Thr Gly Tyr Ile Ala
225                 230                 235                 240

Pro Phe Val Ser Arg Lys Asn Leu Phe Val Leu Ala Asn His Thr Val
                245                 250                 255

Ser Arg Ile Gln Phe Lys Pro Lys Asn Gly Thr Glu Leu Leu Lys Ala
            260                 265                 270

Val Gly Val Glu Trp Tyr Thr Thr Gly Asp Asn Ser Asn Lys Gln Thr
        275                 280                 285

Ile Lys Ala Arg Arg Glu Val Ile Val Ser Ser Gly Ser Ile Gly Ser
    290                 295                 300

Pro Lys Leu Leu Glu Ile Ser Gly Ile Gly Asn Lys Asp Ile Val Thr
305                 310                 315                 320

Ala Ala Gly Val Gln Ser Leu Ile Asp Leu Pro Gly Val Gly Ser Asn
                325                 330                 335

Met Gln Asp His Val His Ala Val Thr Val Ser Thr Thr Asn Ile Thr
            340                 345                 350
```

```
Gly Phe Thr Thr Asp Ser Val Phe Gln Asn Glu Thr Leu Ala Glu Glu
            355                 360                 365

Gln Arg Gln Gln Tyr Tyr Asn Asn Lys Thr Gly Ile Trp Thr Thr Thr
370                 375                 380

Pro Asn Asn Leu Gly Tyr Pro Ser Pro Ser Gln Leu Phe Asp Gly Thr
385                 390                 395                 400

Ser Phe Glu Ser Gly Gln Ala Phe Ala Asn Arg Ile Arg Asn Ser Thr
            405                 410                 415

Asp Gln Trp Ala Glu Tyr Tyr Ala Ser Thr Asn Ala Thr Asn Ile Glu
                420                 425                 430

Leu Leu Lys Lys Gln Tyr Ala Ile Val Ala Ser Arg Tyr Glu Glu Asn
            435                 440                 445

Tyr Leu Ser Pro Ile Glu Ile Asn Phe Thr Pro Gly Tyr Gly Gly Thr
        450                 455                 460

Thr Asp Val Asp Leu Lys Asn Asn Lys Tyr Gln Thr Val Asn His Val
465                 470                 475                 480

Leu Ile Ala Pro Leu Ser Arg Gly Tyr Thr His Ile Asn Ser Ser Asn
                485                 490                 495

Ile Glu Asp Pro Val Val Ile Asn Pro Gln Tyr Tyr Thr His Pro Met
            500                 505                 510

Asp Val Asp Val His Ile Ala Ser Thr Lys Leu Ala Arg Arg Ile Leu
        515                 520                 525

Gly Ala Glu Pro Gly Leu Ala Ser Ile Asn Ser Gly Glu Ile Gln Pro
    530                 535                 540

Gly Ser Asn Ile Thr Ser Asp Glu Asp Val Lys Gln Trp Leu Ala Asp
545                 550                 555                 560

Asn Val Arg Ser Asp Trp His Pro Val Gly Thr Cys Ala Met Leu Pro
                565                 570                 575

Arg Glu Leu Gly Gly Val Val Asp Pro Asn Leu Leu Val Tyr Gly Thr
            580                 585                 590

Ala Asn Leu Arg Val Val Asp Ala Ser Ile Met Pro Leu Glu Ile Ser
        595                 600                 605

Ser His Leu Met Gln Pro Thr Tyr Gly Val Ala Glu Lys Ala Ala Asp
    610                 615                 620

Ile Ile Lys Met Ser Arg Lys Asn Asn Asn
625                 630                 635

<210> SEQ ID NO 3
<211> LENGTH: 633
<212> TYPE: PRT
<213> ORGANISM: Mucor subtilissimus

<400> SEQUENCE: 3

Met Arg Leu Ser Leu Ala Ile Leu Ser Leu Thr Ser Ala Leu Val Thr
1               5                   10                  15

Val Thr Ser Ala Gln Gln Asn Gly Thr Ser Asn Asp Thr Tyr Asp Tyr
            20                  25                  30

Val Ile Val Gly Gly Gly Val Gly Gly Leu Ser Leu Ala Ser Arg Leu
        35                  40                  45

Ser Glu Asp Lys Gly Val Thr Val Ala Val Leu Glu Ser Gly Pro Tyr
    50                  55                  60

Ala Asp Asp Arg Phe Val Val Tyr Ala Pro Gly Met Tyr Gly Gln Ala
65                  70                  75                  80

Val Gly Thr Glu Leu Cys Pro Leu Leu Pro Thr Val Pro Gln Val Gly
                85                  90                  95
```

```
Met Asn Asn Arg Thr Ile Thr Ile Ala Thr Gly Arg Leu Leu Gly Gly
            100                 105                 110

Gly Ser Ala Val Asn Gly Leu Val Trp Thr Arg Gly Ala Met Lys Asp
        115                 120                 125

Phe Asp Ala Trp Glu Glu Leu Gly Asn Pro Gly Trp Asn Gly Lys Thr
130                 135                 140

Met Phe Lys Tyr Phe Lys Lys Ile Glu Asn Phe His Pro Pro Thr Glu
145                 150                 155                 160

Glu Gln Val Gln Tyr Gly Ala Thr Tyr Gln Lys Asn Val His Gly Ser
                165                 170                 175

Gly Gly Pro Ile Asp Ile Ser Phe Pro Val Phe Glu Phe Pro Gln Ser
            180                 185                 190

Ala Asn Trp Asn Ala Ser Leu Ala Tyr Leu Asn Phe Thr His Gln Gln
        195                 200                 205

Asp Leu Leu Asn Gly Ser Leu His Gly Tyr Ser Thr Thr Pro Asn Thr
210                 215                 220

Leu Asn Pro Glu Thr Ala Arg Arg Ala Asp Ala Tyr Ala Gly Tyr Ile
225                 230                 235                 240

Gln Pro Asn Val Asn Arg Thr Asn Leu Ala Val Leu Ala Asn His Thr
                245                 250                 255

Val Ser Arg Ile Gln Phe Glu Lys Ser Asn Gly Ser Gln Pro Leu Lys
            260                 265                 270

Ala Ile Gly Val Glu Trp Tyr Thr Thr Gly Gly Asp Lys Ser Thr Lys
        275                 280                 285

Gln Thr Ile Lys Ala Arg Arg Glu Val Ile Ile Ser Ser Gly Ala Ile
290                 295                 300

Gly Ser Pro Lys Leu Leu Glu Val Ser Gly Ile Gly Asn Lys Gln Ile
305                 310                 315                 320

Val Thr Ala Ala Gly Val Glu Ser Leu Ile Asp Leu Pro Gly Val Gly
                325                 330                 335

Ser Asn Met Gln Asp His Val His Ala Val Thr Val Ser Thr Thr Asn
            340                 345                 350

Ile Glu Gly Tyr Thr Thr Asn Ser Val Phe Thr Asn Glu Thr Leu Ala
        355                 360                 365

Gln Glu Gln Lys Asp Leu Tyr Tyr Asn Asn Lys Thr Gly Ile Trp Thr
370                 375                 380

Thr Thr Pro Asn Asn Leu Gly Tyr Pro Ser Pro Ser Gln Leu Phe Thr
385                 390                 395                 400

Asn Thr Thr Phe Arg Ser Gly Lys Gln Phe Ala Ala Met Ile Arg Asn
                405                 410                 415

Ser Thr Asp Lys Tyr Ala Gln Tyr Tyr Ala Ser Thr Lys Asn Ala Thr
            420                 425                 430

Asn Ile Gln Leu Leu Lys Lys Gln Tyr Ala Ile Val Ala Arg Arg Tyr
        435                 440                 445

Glu Glu Asp Tyr Ile Ser Pro Ile Glu Ile Asn Phe Thr Pro Gly Tyr
450                 455                 460

Gly Gly Thr Gly Glu Val Asp Leu Gln Asn Asn Lys Tyr Gln Thr Val
465                 470                 475                 480

Asn His Val Leu Val Ala Pro Leu Ser Arg Gly Tyr Thr His Ile Asn
                485                 490                 495

Ser Ser Asp Ile Glu Asp Pro Val Val Ile Asp Pro Gln Tyr Tyr Ser
            500                 505                 510
```

His Pro Leu Asp Val Asp Val His Val Ala Ser Thr Gln Leu Ala Arg
            515                 520                 525

Ser Ile Leu Asn Ala Pro Ala Leu Ala Ala Ile Asn Ser Gly Glu Val
        530                 535                 540

Glu Pro Gly Glu Lys Ile Gln Thr Asp Gln Asp Val Arg Lys Trp Leu
545                 550                 555                 560

Ser Asp Asn Val Arg Ser Asp Trp His Pro Val Gly Thr Cys Ala Met
                565                 570                 575

Leu Pro Lys Gly Leu Gly Gly Val Val Asp Ser Asn Leu Lys Val Tyr
            580                 585                 590

Gly Thr Ala Asn Leu Arg Val Val Asp Ala Ser Ile Ile Pro Leu Glu
        595                 600                 605

Ile Ser Ser His Leu Met Gln Pro Val Tyr Ala Val Ser Glu Arg Ala
610                 615                 620

Ala Asp Ile Ile Lys Gly Ser Arg Asn
625                 630

<210> SEQ ID NO 4
<211> LENGTH: 637
<212> TYPE: PRT
<213> ORGANISM: Circinella simplex

<400> SEQUENCE: 4

Met Lys Ile Ser Ala Ala Val Val Thr Ile Val Ala Phe Ala Ser
1               5                   10                  15

Val Ala Thr Ala Gln Gln Gln Asn Thr Ser Glu Thr Asn Thr Tyr Asp
            20                  25                  30

Tyr Val Ile Val Gly Gly Gly Val Gly Gly Leu Ala Leu Ala Ser Arg
        35                  40                  45

Leu Ser Glu Asn Lys Gly Val Ser Val Ala Val Leu Glu Ala Gly Pro
    50                  55                  60

Tyr Ala Gly Asp Gln Phe Val Val Tyr Ala Pro Gly Met Tyr Gly Gln
65                  70                  75                  80

Ala Val Gly Thr Asp Leu Cys Pro Leu Leu Pro Thr Thr Pro Gln Glu
                85                  90                  95

Asn Met Gly Asn Arg Ser Leu Ser Ile Ala Thr Gly Lys Leu Leu Gly
            100                 105                 110

Gly Gly Ser Ser Val Asn Gly Leu Val Trp Thr Arg Gly Gly Leu Lys
        115                 120                 125

Asp Phe Asp Ala Trp Glu Glu Leu Gly Asn Pro Gly Trp Asn Gly Ala
    130                 135                 140

Ser Met Phe Asn Tyr Phe Lys Lys Val Glu Asn Phe Thr Pro Pro Thr
145                 150                 155                 160

Pro Ala Gln Ala Ala Tyr Gly Ala Thr Tyr Gln Lys Asn Ala His Gly
                165                 170                 175

Thr Lys Gly Pro Met Asp Val Ser Phe Thr Asn Phe Glu Phe Pro Gln
            180                 185                 190

Ser Gly Asn Trp Asn Ala Ser Leu Asn Ala Val Gly Phe Thr Ala Val
        195                 200                 205

Pro Asp Leu Leu Asn Gly Thr Leu His Gly Tyr Ser Thr Thr Pro Asn
    210                 215                 220

Ile Leu Asp Pro Val Asn Ala Arg Arg Ala Asp Ala Tyr Ala Gly Tyr
225                 230                 235                 240

Ile Lys Pro Tyr Ile Ser Arg Asn Asn Leu Ala Val Leu Ala Asn His
                245                 250                 255

```
Thr Val Ser Arg Ile Gln Phe Ala Pro Gln Ser Gly Ser Gln Pro Leu
            260                 265                 270

Arg Ala Thr Gly Val Glu Trp Tyr Pro Thr Gly Asp Lys Ser Gln Lys
            275                 280                 285

Gln Val Leu Asn Ala Arg Tyr Glu Val Ile Leu Ser Ser Gly Ala Ile
            290                 295                 300

Gly Ser Pro Lys Leu Leu Glu Leu Ser Gly Ile Gly Asn Lys Asp Ile
305                 310                 315                 320

Val Ala Ala Ala Gly Ile Gln Ser Leu Leu Asp Leu Pro Val Gly
                325                 330                 335

Ser Asn Met Gln Asp His Val His Ala Val Thr Val Ser Thr Thr Asn
            340                 345                 350

Ile Thr Gly Tyr Thr Thr Asn Ser Ile Phe Thr Asn Asp Ala Leu Ala
            355                 360                 365

Ala Glu Glu Arg Gln Glu Tyr Asp Asn Asn Lys Thr Gly Ile Tyr Thr
            370                 375                 380

Thr Thr Pro Asn Asn Leu Gly Tyr Pro Ser Pro Ser Gln Leu Phe Arg
385                 390                 395                 400

Gly Thr Ser Phe Val Ser Gly Lys Gln Phe Ala Ala Arg Ile Arg Asn
                405                 410                 415

Thr Thr Asp Glu Trp Ala Glu Arg Tyr Ala Ala Asp Asn Ala Thr Asn
            420                 425                 430

Ala Glu Leu Leu Lys Lys Gln Tyr Ala Ile Ile Ala Ser Arg Tyr Glu
            435                 440                 445

Glu Asp Tyr Leu Ser Pro Ile Glu Ile Asn Leu Thr Pro Gly Tyr Gly
            450                 455                 460

Gly Thr Ala Asp Val Asp Leu Thr Asn Asn Lys Tyr Gln Thr Val Asn
465                 470                 475                 480

His Val Leu Ile Ala Pro Leu Ser Arg Gly Tyr Thr His Ile Lys Ser
                485                 490                 495

Ala Asp Ile Glu Asp Ala Val Asp Ile Asn Pro Gln Tyr Tyr Ser His
            500                 505                 510

Pro Met Asp Val Asp Val His Val Ala Ser Thr Lys Leu Ala Arg Glu
            515                 520                 525

Ile Ile Ser Ala Ser Pro Gly Leu Gly Asp Ile Asn Ser Gly Glu Thr
            530                 535                 540

Glu Pro Gly Lys Glu Ile Thr Ser Asp Ser Asp Val Arg Lys Trp Leu
545                 550                 555                 560

Ala Asp Asn Val Arg Ser Asp Trp His Pro Val Gly Thr Cys Ala Met
                565                 570                 575

Leu Pro Lys Glu Leu Gly Gly Val Val Asp Pro Asn Leu Lys Val Tyr
            580                 585                 590

Gly Thr Ser Asn Leu Arg Val Val Asp Ala Ser Val Met Pro Leu Glu
            595                 600                 605

Val Ser Ser His Leu Met Gln Pro Thr Phe Gly Ile Ala Glu Lys Ala
            610                 615                 620

Ala Asp Ile Ile Lys Ser Ala Asn Lys Lys Arg Ser Asn
625                 630                 635

<210> SEQ ID NO 5
<211> LENGTH: 593
<212> TYPE: PRT
<213> ORGANISM: Metarhizium sp. F2114
```

```
<400> SEQUENCE: 5

Met Phe Arg Pro Leu Val Leu Leu Ser Thr Leu Thr Ala Thr Leu Ala
1               5                   10                  15

Cys Pro Thr Arg Gln Ile Lys Thr Ala Ser Lys Tyr Asp Tyr Ile Val
            20                  25                  30

Ile Gly Gly Gly Thr Ser Gly Leu Val Ile Ala Asn Arg Leu Ser Glu
                35                  40                  45

Asp Arg Asn Val Ser Val Leu Val Ile Glu Ala Gly Lys Ser Val Leu
50                  55                  60

Asn Asn Ala Asn Val Thr Asp Val Asp Gly Tyr Gly Leu Ala Phe Gly
65                  70                  75                  80

Thr Asp Ile Asp Trp Gln Tyr Lys Ser Val Asn Gln Thr Tyr Gly Gly
                85                  90                  95

Asn Lys Glu Leu Val Phe Arg Ala Gly Lys Ala Val Ala Gly Thr Ser
                100                 105                 110

Ala Ile Asn Gly Met Ala Tyr Thr Arg Ala Glu Asp Val Gln Ile Asp
            115                 120                 125

Ala Trp Gln Thr Ile Gly Asn Glu Gly Trp Thr Trp Glu Lys Leu Leu
130                 135                 140

Pro Tyr Tyr Leu Gln Ser Glu Lys Leu Thr Ile Pro Ser Gln Ser Gln
145                 150                 155                 160

Val Ser Lys Gly Ala Ser Tyr Asn Ala Ser Leu His Gly Lys Ser Gly
                165                 170                 175

Pro Leu Asp Val Gly Phe Phe Asp Ile Pro Asp Asn Asp Leu Thr Gly
            180                 185                 190

Val Leu Asn Thr Thr Met Asn Gly Leu Gly Ile Pro Trp Val Glu Asp
            195                 200                 205

Val Asn Gly Gly Lys Met Arg Gly Phe Asn Ile Phe Pro Ser Thr Ile
210                 215                 220

Asn Val Ala Ala Asn Val Arg Glu Asp Ala Ala Arg Ala Tyr Tyr Trp
225                 230                 235                 240

Pro Val Ala Ser Arg Gln Asn Leu His Leu Leu Val Asp Thr Phe Val
                245                 250                 255

Asn Arg Ile Ile Trp Gln Asp Lys Ala Asn Asn Ser Asp His Val Thr
            260                 265                 270

Ala Ser Gly Val Glu Val Thr Leu Ala Asn Gly Thr Thr Ser Val Val
            275                 280                 285

Ser Ala Asn Arg Glu Val Ile Val Ser Ala Gly Ala Leu Lys Ser Pro
290                 295                 300

Gly Ile Leu Glu Leu Ser Gly Ile Gly Asp Ala Thr Leu Leu Glu Lys
305                 310                 315                 320

His Glu Ile Pro Val Gln Val Asn Leu Pro Thr Val Gly Glu Asn Leu
                325                 330                 335

Gln Asp Gln Thr Asn Ala Gln Ser Gly Ala Ala Ile Lys Ala Asn Met
            340                 345                 350

Thr Ser Ala Thr His Val Val Tyr Pro Asn Val Tyr Asp Ile Tyr Gly
            355                 360                 365

Asn Gln Thr Asp Tyr Leu Ala Leu Ser Met Gln Lys Lys Ile Lys Asp
            370                 375                 380

Tyr Ala Arg Ala Thr Ala Glu Val Ser Asn Gly Ile Met Lys Ala Ser
385                 390                 395                 400

Asp Leu Glu Ala Leu Phe Gln Val Gln Tyr Asp Leu Ile Phe Lys Gln
                405                 410                 415
```

-continued

```
Arg Thr Pro Ile Ala Glu Ile Leu Tyr Ser Ala Arg Gly Asp Asn Ala
                420                 425                 430

Ile Ser Ser Glu Tyr Trp Thr Leu Leu Pro Phe Ala Arg Gly Asn Val
            435                 440                 445

His Ile Ser Ser Ser Asp Pro Thr Ala Met Pro Ile Ile Asn Pro Asn
        450                 455                 460

Phe Phe Met Leu Asp Trp Asp Leu Asp Ser Met Ile Ala Val Ala Lys
465                 470                 475                 480

Tyr Ile Arg Thr Ser Phe Ser Ala Gly Pro Leu Gly Lys Leu Val Glu
                485                 490                 495

Gly Val Thr Ile Pro Asp Pro Ala Val Ile Asp Tyr Ala Thr Asp
            500                 505                 510

Ala Ala Trp Lys Glu Trp Leu Leu Asp Gly His Tyr Arg Ser Asn Phe
        515                 520                 525

His Pro Leu Gly Thr Ala Ala Met Met Pro Arg Glu Lys Gly Gly Val
530                 535                 540

Val Asp Asn Lys Leu Met Val Tyr Gly Thr Ser Asn Val Arg Val Val
545                 550                 555                 560

Asp Ala Ser Ile Leu Pro Tyr Gln Val Cys Gly His Leu Thr Ser Thr
                565                 570                 575

Leu Tyr Ala Met Ala Glu Leu Thr Ala Glu Leu Ile Lys His Asp Ser
            580                 585                 590

Ala

<210> SEQ ID NO 6
<211> LENGTH: 635
<212> TYPE: PRT
<213> ORGANISM: Colletotrichum

<400> SEQUENCE: 6

Met Pro Leu Phe Arg Gln Ser Lys Ser Gln Pro Arg Trp Pro Gly Val
1               5                   10                  15

Ala Ser Ala Val Phe Leu Ala Ala Ser Ser Val Ala Asn Ala Tyr Ala
                20                  25                  30

Ile Pro Arg Asp Ile Lys Pro Ser Glu Leu Leu Gln Ser Tyr Asp Tyr
            35                  40                  45

Val Ile Val Gly Gly Gly Thr Ala Gly Leu Thr Val Ala Asp Arg Leu
        50                  55                  60

Thr Glu Asp Pro Asn Thr Thr Val Leu Val Leu Glu Ala Gly Gly Trp
65                  70                  75                  80

Ser Asn Met Thr Asp Asn Leu Met Ala Tyr Val Ala Gly Arg Ser Gly
                85                  90                  95

Arg Ile Leu Trp Pro Gly Leu Gln Ser Val Pro Gln Glu His Leu Asn
            100                 105                 110

Gly Arg Thr Asn Thr Val Ser Val Ala Arg Gln Val Gly Gly Gly Ser
        115                 120                 125

Ala Ile Asn Ala Met Ile Thr Met Arg Gly Ser Ala Glu Asp Tyr Asp
    130                 135                 140

Arg Trp Ala Thr Leu Phe Gly Pro Glu Ala Gln Arg Gly Thr Ala Asp
145                 150                 155                 160

Trp Ser Trp Asp Gly Ile Leu Pro Phe Phe Lys Lys Ala Leu His Phe
                165                 170                 175

Thr Glu Pro Pro Pro Glu Leu Thr Asp Asn Phe Asp Ile Lys Tyr Asp
            180                 185                 190
```

```
Ala Ser Tyr Trp Gly Asp Ser Ser Glu Leu Tyr Ala Gly Trp Pro Arg
        195                 200                 205

Phe Tyr Tyr Pro Gly Val Thr Pro Leu Leu Glu Ala Phe Lys Glu Ile
        210                 215                 220

Glu Gly Val Glu Phe Pro Pro Asp Ser Gly Ala Gly Gln Pro Gly Val
225                 230                 235                 240

Tyr Trp Phe Pro Ala Phe Met Asp Pro Arg Thr Val Thr Arg Ser Tyr
                245                 250                 255

Ala Ala Thr Gly His Tyr Leu Asn Val Asn Ala Thr Arg Gln Asn Tyr
            260                 265                 270

His Leu Leu Ile Asn Ser Gln Ala Arg Lys Leu Ile Leu Asp Asp Asn
        275                 280                 285

Leu Thr Ala Thr Gly Val Glu Phe Pro Leu Ala Asn Asn Thr Leu Phe
    290                 295                 300

Thr Val Asn Ala Arg Lys Glu Val Ile Leu Ser Ala Gly Thr Val His
305                 310                 315                 320

Thr Pro Gln Leu Leu Gln Leu Ser Gly Val Gly Pro Lys Lys Leu Leu
                325                 330                 335

Glu Glu Ala Gly Ile Asp Val Arg Val Asp Leu Pro Val Gly Val Gln
            340                 345                 350

Asn Phe Gln Asp His Ser Ser Leu Ser Thr Val Asn Ile Thr Leu Ser
        355                 360                 365

Lys Ile Thr Ser Ile His Pro Asn Pro Lys Asp Leu Val Asp Gly Asn
    370                 375                 380

Asp Phe Lys Thr Trp Ala Asp Glu Val Trp Gln Ala Asn Lys Thr Gly
385                 390                 395                 400

Pro Tyr Ser Ile Ser Trp Thr Asn Leu Ala Gly Trp Leu Pro Phe Thr
                405                 410                 415

Val Ile Ser Asp Lys Ala Asp Glu Leu Ala Thr Lys Leu Glu Gln Gln
            420                 425                 430

Asp Phe Ala Ser Leu Leu Pro Ala Gly Thr Asp Ala Thr Val Val Ala
        435                 440                 445

Gly Phe Glu Ala Gln Met Lys Leu Leu Ala Ala Gln Met Arg Ser Lys
    450                 455                 460

Asn Thr Ala Phe Thr Arg Tyr Gln Leu Ile Ala Glu His Gly Val Gln
465                 470                 475                 480

Gly Pro Val Gly Leu Gln Ser Phe Ser Arg Gly Thr Ile Asn Ile Asn
                485                 490                 495

Thr Thr Asn Pro Trp Asn Thr Glu Pro Val Ile Asp Tyr Arg Val Leu
            500                 505                 510

Ser Asn Pro Leu Glu Ala Asp Tyr Phe Val Glu Ser Ile Lys Phe Leu
        515                 520                 525

Arg Arg Tyr Asn Phe Glu Thr Ser Leu Ala Ser Lys Phe Glu Pro Val
    530                 535                 540

Glu Tyr Val Pro Gly Pro Asp Val Thr Ser Asp Glu Asp Leu Lys Ala
545                 550                 555                 560

Tyr Ile Ala Arg Ala Leu Ser Pro Ser Asp Tyr His Pro Val Gly Thr
                565                 570                 575

Ala Ser Met Leu Pro Leu Asn Leu Gly Gly Val Val Asp Gln Thr Leu
            580                 585                 590

Arg Val Tyr Gly Val Lys Asn Leu Arg Val Val Asp Ala Ser Val Met
        595                 600                 605
```

```
Pro Met Val Pro Gly Ala Asn Thr Cys Gln Pro Thr Tyr Ala Leu Ala
    610                 615                 620

Glu Lys Ala Ser Glu Ile Ile Lys Gln Gly Ile
625                 630                 635

<210> SEQ ID NO 7
<211> LENGTH: 367
<212> TYPE: PRT
<213> ORGANISM: Lactococcus lactis

<400> SEQUENCE: 7

Met Glu Lys Thr Tyr Gln Ala Gly Thr Asn Glu Gly Ile Val Asp Phe
1               5                   10                  15

Ile Asn Met Glu Asp Leu Glu Ile Ala Ala Ser Gln Val Ile Pro Ala
                20                  25                  30

Gly Gly Tyr Gly Tyr Ile Ser Ser Gly Ala Gly Asp Leu Phe Thr Tyr
            35                  40                  45

Gln Glu Asn Glu Arg Ala Phe Asn His Gln Leu Ile Ile Pro His Val
        50                  55                  60

Leu Arg Asp Val Glu Leu Pro Asp Thr Thr His Phe Asp Glu Glu
65                  70                  75                  80

Thr Leu Thr Ala Pro Ile Ile Met Ala Pro Val Ala Ala His Gly Leu
                85                  90                  95

Ala His Val Lys Ala Glu Lys Ala Ser Ala Lys Gly Val Ala Asp Phe
            100                 105                 110

Gly Thr Ile Tyr Thr Ala Ser Ser Tyr Ala Ser Cys Thr Leu Glu Glu
        115                 120                 125

Ile Arg Glu Ala Gly Gly Lys Ala Pro Gln Trp Phe Gln Phe Tyr
130                 135                 140

Met Ser Lys Asp Asn Gly Ile Asn Leu Asp Ile Leu Glu Val Ala Lys
145                 150                 155                 160

Arg Asn Gly Ala Lys Ala Ile Val Leu Thr Ala Asp Ala Thr Val Gly
                165                 170                 175

Gly Asn Arg Glu Thr Asp Arg Arg Asn Gly Phe Thr Phe Pro Leu Pro
            180                 185                 190

Met Pro Ile Val Gln Ala Tyr Gln Ser Gly Val Gly Gln Thr Met Asp
        195                 200                 205

Ala Val Tyr Lys Ser Ser Lys Gln Lys Leu Ser Pro Lys Asp Val Glu
    210                 215                 220

Phe Ile Ala Ala His Ser Asp Leu Pro Val Tyr Val Lys Gly Val Gln
225                 230                 235                 240

Ser Glu Glu Asp Val Tyr Arg Ser Leu Glu Ser Gly Ala Gly Gly Ile
                245                 250                 255

Trp Val Ser Asn His Gly Gly Arg Gln Leu Asp Gly Gly Pro Ala Ala
            260                 265                 270

Phe Asp Ser Leu Gln Tyr Val Ala Asp Ala Val Asp Lys Arg Val Pro
        275                 280                 285

Ile Val Phe Asp Ser Gly Val Arg Gly Gln His Val Phe Lys Ala
290                 295                 300

Ile Ala Ser Gly Ala Asp Leu Val Ala Ile Gly Arg Pro Val Ile Tyr
305                 310                 315                 320

Gly Leu Ser Leu Gly Gly Ser Thr Gly Val Arg Gln Val Phe Asp Phe
                325                 330                 335
```

```
Phe Lys Thr Glu Leu Glu Met Val Met Gln Leu Ala Gly Thr Gln Thr
                340                 345                 350

Val Glu Asp Ile Lys Lys Ile Lys Leu Arg Glu Asn Arg Phe Ile
            355                 360                 365
```